(12) United States Patent
Mickelsen

(10) Patent No.: US 12,390,272 B2
(45) Date of Patent: Aug. 19, 2025

(54) METHODS AND APPARATUS FOR SELECTIVE TISSUE ABLATION

(71) Applicant: Boston Scientific Scimed, Inc., Maple Grove, MN (US)

(72) Inventor: Steven R. Mickelsen, Iowa City, IA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/674,607

(22) Filed: May 24, 2024

(65) Prior Publication Data

US 2024/0307116 A1 Sep. 19, 2024

Related U.S. Application Data

(63) Continuation of application No. 17/349,299, filed on Jun. 16, 2021, which is a continuation of application
(Continued)

(51) Int. Cl.
*A61B 18/14* (2006.01)
*A61B 5/0538* (2021.01)
(Continued)

(52) U.S. Cl.
CPC ........ *A61B 18/1492* (2013.01); *A61B 5/0538* (2013.01); *A61N 1/327* (2013.01);
(Continued)

(58) Field of Classification Search
CPC ............ A61B 18/1492; A61B 18/1815; A61B 2018/0022; A61B 2018/00267;
(Continued)

(56) References Cited

U.S. PATENT DOCUMENTS 4,200,104 A 4/1980 Harris
4,470,407 A 9/1984 Hussein
(Continued)

FOREIGN PATENT DOCUMENTS

EP 1042990 A1 10/2000
EP 1125549 A2 8/2001
(Continued)

OTHER PUBLICATIONS

Du Pre, B.C. et al., "Minimal coronary artery damage by myocardial electroporation ablation," Europace, 15(1):144-149 (2013).
(Continued)

*Primary Examiner* — Khadijeh A Vahdat
(74) *Attorney, Agent, or Firm* — Nelson Mullins Riley & Scarborough LLP

(57) ABSTRACT

Catheter systems and methods for the selective and rapid application of DC voltage to drive irreversible electroporation are disclosed herein. In some embodiments, an apparatus includes a voltage pulse generator and an electrode controller. The voltage pulse generator is configured to produce a pulsed voltage waveform. The electrode controller is configured to be operably coupled to the voltage pulse generator and a medical device including a series of electrodes. The electrode controller includes a selection module and a pulse delivery module. The selection module is configured to select a subset of electrodes from the series of electrodes. The selection module is configured identify at least one electrode as an anode and at least one electrode as a cathode. The pulse delivery module is configured to deliver an output signal associated with the pulsed voltage waveform to the subset of electrodes.

19 Claims, 25 Drawing Sheets

Related U.S. Application Data

No. 15/795,062, filed on Oct. 26, 2017, now Pat. No. 11,259,869, which is a continuation of application No. 15/341,512, filed on Nov. 2, 2016, now abandoned, which is a continuation of application No. PCT/US2015/029734, filed on May 7, 2015.

(60) Provisional application No. 61/996,390, filed on May 7, 2014.

(51) Int. Cl.
| | | |
|---|---|---|
| *A61N 1/32* | (2006.01) | |
| *A61N 7/02* | (2006.01) | |
| *A61B 17/00* | (2006.01) | |
| *A61B 18/00* | (2006.01) | |
| *A61B 18/12* | (2006.01) | |
| *A61B 18/18* | (2006.01) | |
| *A61N 1/04* | (2006.01) | |

(52) U.S. Cl.
CPC .... *A61N 7/022* (2013.01); *A61B 2017/00026* (2013.01); *A61B 2017/00154* (2013.01); *A61B 2018/0022* (2013.01); *A61B 2018/00267* (2013.01); *A61B 2018/00351* (2013.01); *A61B 2018/00404* (2013.01); *A61B 2018/00577* (2013.01); *A61B 2018/00613* (2013.01); *A61B 2018/00654* (2013.01); *A61B 2018/00827* (2013.01); *A61B 2018/00839* (2013.01); *A61B 2018/00875* (2013.01); *A61B 2018/00892* (2013.01); *A61B 2018/00994* (2013.01); *A61B 2018/124* (2013.01); *A61B 2018/1467* (2013.01); *A61B 18/1815* (2013.01); *A61B 2218/002* (2013.01); *A61B 2576/023* (2013.01); *A61N 1/0412* (2013.01)

(58) Field of Classification Search
CPC ........... A61B 2018/00351; A61B 2018/00404; A61B 2018/00577; A61B 2018/00613; A61B 2018/00654; A61B 2018/00827; A61B 2018/00839; A61B 2018/00875; A61B 2018/00892; A61B 2018/00994; A61B 2018/124; A61B 2018/1467; A61B 2218/002; A61B 2017/00026; A61B 2017/00154; A61N 1/0412; A61N 1/327; A61N 7/022

See application file for complete search history.

(56) References Cited

U.S. PATENT DOCUMENTS

| | | | |
|---|---|---|---|
| 4,739,759 | A | 4/1988 | Rexroth et al. |
| 5,234,004 | A | 8/1993 | Hascoet et al. |
| 5,242,441 | A | 9/1993 | Avitall |
| 5,257,635 | A | 11/1993 | Langberg |
| 5,281,213 | A | 1/1994 | Milder et al. |
| 5,304,214 | A | 4/1994 | Deford et al. |
| 5,306,296 | A | 4/1994 | Wright et al. |
| 5,334,193 | A | 8/1994 | Nardella |
| 5,341,807 | A | 8/1994 | Nardella |
| 5,342,301 | A | 8/1994 | Saab |
| 5,398,683 | A | 3/1995 | Edwards et al. |
| 5,443,463 | A | 8/1995 | Stern et al. |
| 5,454,370 | A | 10/1995 | Avitall |
| 5,515,848 | A | 5/1996 | Corbett et al. |
| 5,531,685 | A | 7/1996 | Hemmer et al. |
| 5,545,161 | A | 8/1996 | Imran |
| 5,558,091 | A | 9/1996 | Acker et al. |
| 5,578,040 | A | 11/1996 | Smith |
| 5,617,854 | A | 4/1997 | Munsif |
| 5,624,430 | A | 4/1997 | Eton et al. |
| 5,662,108 | A | 9/1997 | Budd et al. |
| 5,667,491 | A | 9/1997 | Pliquett et al. |
| 5,672,170 | A | 9/1997 | Cho et al. |
| 5,700,243 | A | 12/1997 | Narciso, Jr. |
| 5,702,438 | A | 12/1997 | Avitall |
| 5,706,823 | A | 1/1998 | Wodlinger |
| 5,722,400 | A | 3/1998 | Ockuly et al. |
| 5,722,402 | A | 3/1998 | Swanson et al. |
| 5,749,914 | A | 5/1998 | Janssen |
| 5,779,699 | A | 7/1998 | Lipson |
| 5,788,692 | A | 8/1998 | Campbell et al. |
| 5,810,762 | A | 9/1998 | Hofmann |
| 5,833,710 | A | 11/1998 | Jacobson |
| 5,836,874 | A | 11/1998 | Swanson et al. |
| 5,836,942 | A | 11/1998 | Netherly et al. |
| 5,836,947 | A | 11/1998 | Fleischman et al. |
| 5,843,154 | A | 12/1998 | Osypka |
| 5,849,028 | A | 12/1998 | Chen |
| 5,863,291 | A | 1/1999 | Schaer |
| 5,868,736 | A | 2/1999 | Swanson et al. |
| 5,871,523 | A | 2/1999 | Fleischman et al. |
| 5,876,336 | A | 3/1999 | Swanson et al. |
| 5,885,278 | A | 3/1999 | Fleischman |
| 5,895,404 | A | 4/1999 | Ruiz |
| 5,899,917 | A | 5/1999 | Edwards et al. |
| 5,904,709 | A | 5/1999 | Arndt et al. |
| 5,916,158 | A | 6/1999 | Webster, Jr. |
| 5,916,213 | A | 6/1999 | Haissaguerre et al. |
| 5,921,924 | A | 7/1999 | Avitall |
| 5,928,269 | A | 7/1999 | Alt |
| 5,928,270 | A | 7/1999 | Ramsey, III |
| 6,002,955 | A | 12/1999 | Willems et al. |
| 6,006,131 | A | 12/1999 | Cooper et al. |
| 6,009,351 | A | 12/1999 | Flachman |
| 6,014,579 | A | 1/2000 | Pomeranz et al. |
| 6,029,671 | A | 2/2000 | Stevens et al. |
| 6,033,403 | A | 3/2000 | Tu et al. |
| 6,035,238 | A | 3/2000 | Ingle et al. |
| 6,045,550 | A | 4/2000 | Simpson et al. |
| 6,059,779 | A | 5/2000 | Mills |
| 6,068,653 | A | 5/2000 | LaFontaine |
| 6,071,274 | A | 6/2000 | Thompson et al. |
| 6,071,281 | A | 6/2000 | Burnside et al. |
| 6,074,389 | A | 6/2000 | Levine et al. |
| 6,076,012 | A | 6/2000 | Swanson et al. |
| 6,090,104 | A | 7/2000 | Webster, Jr. |
| 6,096,036 | A | 8/2000 | Bowe et al. |
| 6,113,595 | A | 9/2000 | Muntermann |
| 6,119,041 | A | 9/2000 | Pomeranz et al. |
| 6,120,500 | A | 9/2000 | Bednarek et al. |
| 6,146,381 | A | 11/2000 | Bowe et al. |
| 6,164,283 | A | 12/2000 | Lesh |
| 6,167,291 | A | 12/2000 | Barajas et al. |
| 6,171,305 | B1 | 1/2001 | Sherman |
| 6,216,034 | B1 | 4/2001 | Hofmann et al. |
| 6,219,582 | B1 | 4/2001 | Hofstad et al. |
| 6,223,085 | B1 | 4/2001 | Dann et al. |
| 6,231,518 | B1 | 5/2001 | Grabek et al. |
| 6,245,064 | B1 | 6/2001 | Lesh et al. |
| 6,251,107 | B1 | 6/2001 | Schaer |
| 6,251,128 | B1 | 6/2001 | Knopp et al. |
| 6,270,476 | B1 | 8/2001 | Santoianni et al. |
| 6,272,384 | B1 | 8/2001 | Simon et al. |
| 6,287,306 | B1 | 9/2001 | Kroll et al. |
| 6,314,963 | B1 | 11/2001 | Vaska et al. |
| 6,322,559 | B1 | 11/2001 | Daulton et al. |
| 6,350,263 | B1 | 2/2002 | Wetzig et al. |
| 6,370,412 | B1 | 4/2002 | Armoundas et al. |
| 6,391,024 | B1 | 5/2002 | Sun et al. |
| 6,447,505 | B2 | 9/2002 | McGovern et al. |
| 6,464,699 | B1 | 10/2002 | Swanson |
| 6,470,211 | B1 | 10/2002 | Ideker et al. |
| 6,502,576 | B1 | 1/2003 | Lesh |
| 6,503,247 | B2 | 1/2003 | Swartz et al. |
| 6,517,534 | B1 | 2/2003 | McGovern et al. |
| 6,527,724 | B1 | 3/2003 | Fenici |
| 6,527,767 | B2 | 3/2003 | Wang et al. |
| 6,592,581 | B2 | 7/2003 | Bowe |
| 6,595,991 | B2 | 7/2003 | Toellner et al. |

(56) References Cited

U.S. PATENT DOCUMENTS

| | | |
|---|---|---|
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,282,057 B2 | 10/2007 | Surti et al. |
| 7,285,116 B2 | 10/2007 | De et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |

(56) References Cited

U.S. PATENT DOCUMENTS

| | | |
|---|---|---|
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Prestel |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2002/0198519 A1 | 12/2002 | Qin et al. |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Maynard |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0236419 A1 | 11/2004 | Milo |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2005/0288730 A1 | 12/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066957 A1 | 3/2007 | Demarais et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0172104 A1 | 7/2008 | Kieval et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0249518 A1 | 10/2008 | Warnking et al. |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2008/0319436 A1 | 12/2008 | Daniel et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076409 A1 | 3/2009 | Wu et al. |
| 2009/0076500 A1 | 3/2009 | Azure |
| 2009/0105654 A1 | 4/2009 | Kurth et al. |
| 2009/0138009 A1 | 5/2009 | Viswanathan et al. |

(56) References Cited

U.S. PATENT DOCUMENTS

| | | |
|---|---|---|
| 2009/0149917 A1 | 6/2009 | Whitehurst et al. |
| 2009/0163905 A1 | 6/2009 | Winkler et al. |
| 2009/0198300 A1 | 8/2009 | Zhang et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0292342 A1* | 11/2009 | Rubinsky ............ A61N 1/0412 607/72 |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0204619 A1 | 8/2010 | Rosenberg |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0305462 A1 | 12/2010 | Callas et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0095461 A1 | 4/2012 | Herscher et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1* | 7/2013 | Neal, II ............... A61B 18/00 606/41 |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276712 A1 | 9/2014 | Mallin et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |

(56) References Cited

U.S. PATENT DOCUMENTS

| | | |
|---|---|---|
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1* | 11/2015 | Cosman, Jr. .......... A61B 34/10 606/35 |
| 2015/0321021 A1 | 11/2015 | Tandri et al. |
| 2015/0327944 A1 | 11/2015 | Neal et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0168511 A1 | 6/2018 | Hall et al. |
| 2018/0184982 A1 | 7/2018 | Basu et al. |
| 2018/0193090 A1 | 7/2018 | De et al. |
| 2018/0200497 A1 | 7/2018 | Mickelsen |
| 2018/0289417 A1 | 10/2018 | Schweitzer et al. |
| 2018/0303488 A1 | 10/2018 | Hill |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0038171 A1 | 2/2019 | Howard |
| 2019/0046791 A1 | 2/2019 | Ebbers et al. |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0183378 A1 | 6/2019 | Mosesov et al. |
| 2019/0209238 A1 | 7/2019 | Jimenez |
| 2019/0223938 A1 | 7/2019 | Arena et al. |
| 2019/0223950 A1 | 7/2019 | Gelbart et al. |
| 2019/0231421 A1 | 8/2019 | Viswanathan et al. |
| 2019/0233809 A1 | 8/2019 | Neal et al. |
| 2019/0256839 A1 | 8/2019 | Neal et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0336207 A1 | 11/2019 | Raju |
| 2019/0376055 A1 | 12/2019 | Davalos et al. |
| 2021/0031020 A1 | 2/2021 | Mickelsen |
| 2022/0000548 A1 | 1/2022 | Mickelsen |

FOREIGN PATENT DOCUMENTS

| | | |
|---|---|---|
| EP | 0797956 B1 | 6/2003 |
| EP | 1340469 A1 | 9/2003 |
| EP | 1127552 B1 | 6/2006 |
| EP | 1803411 A2 | 7/2007 |
| EP | 1009303 B1 | 6/2009 |
| EP | 2213729 A2 | 8/2010 |
| EP | 2382935 A1 | 11/2011 |
| EP | 2425871 A2 | 3/2012 |
| EP | 2532320 A2 | 12/2012 |
| EP | 2587275 A1 | 5/2013 |
| EP | 2663227 A1 | 11/2013 |
| EP | 1909678 B1 | 1/2014 |
| EP | 2217165 B1 | 3/2014 |
| EP | 2376193 B1 | 3/2014 |
| EP | 2708181 A1 | 3/2014 |
| EP | 2777579 A1 | 9/2014 |
| EP | 2777585 A1 | 9/2014 |
| EP | 2934307 A1 | 10/2015 |
| EP | 3056242 A1 | 8/2016 |
| EP | 3111871 A1 | 1/2017 |
| EP | 3151773 B1 | 4/2018 |
| JP | 06-507797 A | 9/1994 |
| JP | 10-510745 A | 10/1998 |
| JP | 2000-508196 A | 7/2000 |
| JP | 2005-516666 A | 6/2005 |
| JP | 2006-506184 A | 2/2006 |
| JP | 2007-325935 A | 12/2007 |
| JP | 2008-538997 A | 11/2008 |
| JP | 2009-500129 A | 1/2009 |
| JP | 2011-509158 A | 3/2011 |
| JP | 2012-050538 A | 3/2012 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |
| WO | 97/25917 A1 | 7/1997 |
| WO | 97/37719 A1 | 10/1997 |
| WO | 99/04851 A1 | 2/1999 |

(56) References Cited

FOREIGN PATENT DOCUMENTS

| | | |
|---|---|---|
| WO | 99/22659 A1 | 5/1999 |
| WO | 99/56650 A1 | 11/1999 |
| WO | 99/59486 A2 | 11/1999 |
| WO | 02/56782 A1 | 7/2002 |
| WO | 2003/053289 A1 | 7/2003 |
| WO | 03/65916 A1 | 8/2003 |
| WO | 2004/045442 A1 | 6/2004 |
| WO | 2004/086994 A1 | 10/2004 |
| WO | 2005/046487 A1 | 5/2005 |
| WO | 2006/115902 A2 | 11/2006 |
| WO | 2007/006055 A2 | 1/2007 |
| WO | 2007/079438 A2 | 7/2007 |
| WO | 2009/082710 A1 | 7/2009 |
| WO | 2009/089343 A1 | 7/2009 |
| WO | 2009/137800 A2 | 11/2009 |
| WO | 2010/014480 A1 | 2/2010 |
| WO | 2011/028310 A1 | 3/2011 |
| WO | 2011/154805 A1 | 12/2011 |
| WO | 2012/051433 A2 | 4/2012 |
| WO | 2012/097067 A1 | 7/2012 |
| WO | 2012/153928 A2 | 11/2012 |
| WO | 2012/156944 A1 | 11/2012 |
| WO | 2013/019385 A1 | 2/2013 |
| WO | 2014/025394 A1 | 2/2014 |
| WO | 2014/031800 A1 | 2/2014 |
| WO | 2014/036439 A2 | 3/2014 |
| WO | 2014/100579 A1 | 6/2014 |
| WO | 2014/160832 A2 | 10/2014 |
| WO | 2015/066322 A1 | 5/2015 |
| WO | 2015/099786 A1 | 7/2015 |
| WO | 2015/103530 A1 | 7/2015 |
| WO | 2015/103574 A1 | 7/2015 |
| WO | 2015/130824 A1 | 9/2015 |
| WO | 2015/140741 A1 | 9/2015 |
| WO | 2015/143327 A1 | 9/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/059027 A1 | 4/2016 |
| WO | 2016/060983 A1 | 4/2016 |
| WO | 2016/081650 A1 | 5/2016 |
| WO | 2016/090175 A1 | 6/2016 |
| WO | 2017/093926 A1 | 6/2017 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/218734 A1 | 12/2017 |
| WO | 2018/005511 A1 | 1/2018 |
| WO | 2018/191149 A1 | 10/2018 |
| WO | 2018/200800 A1 | 11/2018 |
| WO | 2019/118436 A1 | 6/2019 |
| WO | 2019/133606 A1 | 7/2019 |
| WO | 2019/234133 A1 | 12/2019 |

OTHER PUBLICATIONS

Extended European Search Report for European Application No. 15806278.6, dated Feb. 9, 2018, 5 pages.
Extended European Search Report for European Application No. 15806855.1, dated Jan. 3, 2018, 8 pages.
Extended European Search Report for European Application No. 15849844.4, dated May 3, 2018, 8 pages.
Extended European Search Report for European Application No. 16884132.8, dated Jul. 8, 2019, 7 pages.
Extended European Search Report for European Application No. 16884132.8, mailed Jul. 8, 2019, 7 pages.
Extended European Search Report for European Application No. 17736218.3 dated Aug. 23, 2019, 9 pages.
Extended European Search Report for European Application No. 18170210.1, dated May 17, 2019, 11 pages.
Extended European Search Report for European Application No. 18170210.1, mailed May 17, 2019, 11 pages.
Extended European Search Report for European Application No. 18189811.5, dated May 14, 2019, 7 pages.
Extended European Search Report for European Application No. 19182099.2, dated Dec. 13, 2019, 7 pages.
First Office Action for Chinese Application No. 201580006848.8, dated Jan. 29, 2018, 8 pages.
Hobbs, E. P., "Investor Relations Update: Tissue Ablation via Irreversible Electroporation (IRE)," Powerpoint (2004), 16 pages.
International Preliminary Report on Patentability for International Application No. PCT/US2015/010138, dated Jul. 12, 2016, 9 pages.
International Preliminary Report on Patentability for International Application No. PCT/US2015/010223, dated Jul. 12, 2016, 12 pages.
International Search Report and Written Opinion for International Application No. PCT/US2013/031252, dated Jul. 19, 2013, 12 pages.
International Search Report and Written Opinion for International Application No. PCT/US2015/010138, dated Mar. 26, 2015, 14 pages.
International Search Report and Written Opinion for International Application No. PCT/US2015/010223, dated Apr. 10, 2015, 19 pages.
International Search Report and Written Opinion for International Application No. PCT/US2015/029734, dated Nov. 24, 2015, 15 pages.
International Search Report and Written Opinion for International Application No. PCT/US2015/029734, mailed Nov. 24, 2015, 15 pages.
International Search Report and Written Opinion for International Application No. PCT/US2015/031086, dated Oct. 21, 2015, 16 pages.
International Search Report and Written Opinion for International Application No. PCT/US2015/035582, dated Oct. 2, 2015, 17 pages.
International Search Report and Written Opinion for International Application No. PCT/US2015/035592, dated Oct. 2, 2015, 13 pages.
International Search Report and Written Opinion for International Application No. PCT/US2015/055105, dated Mar. 1, 2016, 15 pages.
International Search Report and Written Opinion for International Application No. PCT/US2016/057664, dated Feb. 24, 2017, 11 pages.
International Search Report and Written Opinion for International Application No. PCT/US2017/012099, dated May 18, 2017, 17 pages.
International Search Report and Written Opinion for International Application No. PCT/US2017/012099, mailed May 18, 2017, 17 pages.
International Search Report and Written Opinion for International Application No. PCT/US2017/037609, dated Nov. 8, 2017, 13 pages.
International Search Report and Written Opinion for International Application No. PCT/US2018/029552, dated Jun. 29, 2018, 13 pages.
International Search Report and Written Opinion for International Application No. PCT/US2018/029552, mailed Jun. 29, 2018, 13 pages.
International Search Report and Written Opinion for International Application No. PCT/US2018/029938, dated Aug. 29, 2018, 14 pages.
International Search Report and Written Opinion for International Application No. PCT/US2018/029938, mailed Aug. 29, 2018, 14 pages.
International Search Report and Written Opinion for International Application No. PCT/US2018/050660, dated Nov. 26, 2018, 13 pages.
International Search Report and Written Opinion for International Application No. PCT/US2018/050660, mailed Nov. 26, 2018, 13 pages.
International Search Report and Written Opinion for International Application No. PCT/US2019/014226, dated Apr. 29, 2019, 15 pages.

(56) References Cited

OTHER PUBLICATIONS

International Search Report and Written Opinion for International Application No. PCT/US2019/014226, mailed Apr. 29, 2019, 15 pages.
International Search Report and Written Opinion for International Application No. PCT/US2019/017322, dated May 10, 2019, 15 pages.
International Search Report and Written Opinion for International Application No. PCT/US2019/017322, mailed May 10, 2019, 15 pages.
International Search Report and Written Opinion for International Application No. PCT/US2019/028943, dated Sep. 17, 2019, 17 pages.
International Search Report and Written Opinion for International Application No. PCT/US2019/028943, mailed Sep. 17, 2019, 17 pages.
International Search Report and Written Opinion for International Application No. PCT/US2019/030882, dated Sep. 10, 2019, 17 pages.
International Search Report and Written Opinion for International Application No. PCT/US2019/030882, mailed Sep. 10, 2019, 17 pages.
International Search Report and Written Opinion for International Application No. PCT/US2019/030922, dated Sep. 6, 2019, 12 pages.
International Search Report and Written Opinion for International Application No. PCT/US2019/031135, dated Aug. 5, 2019, 11 pages.
International Search Report and Written Opinion for International Application No. PCT/US2019/031135, mailed Aug. 5, 2019, 11 pages.
International Search Report and Written Opinion received for PCT Patent Application No. PCT/US2013/031252, mailed on Jul. 19, 2013, 15 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Epicardial linear electroporation ablation and lesion size," Heart Rhythm, 11:1465-1470 (2014).
Neven, K. et al., "Myocardial Lesion Size After Epicardial Electroporation Catheter Ablation After Subxiphoid Puncture," Circ Arrhythm Electrophysiol., 7(4): 728-733 (2014).
Neven, K. et al., "Safety and Feasibility of Closed Chest Epicardial Catheter Ablation Using Electroporation," Circ Arrhythm Electrophysiol., 7:913-919 (2014).
Notice of Reasons for Rejection for Japanese Application No. 2015-526522, dated Mar. 6, 2017, 3 pages.
Notice of Reasons for Rejection for Japanese Application No. 2016-544072, dated Oct. 1, 2018,.
Office Action for Canadian Application No. 2,881,462, dated Mar. 19, 2019, 5 pages.
Office Action for European Application No. 13827672.0, dated Feb. 5, 2018, 6 pages.
Office Action for European Application No. 15701856.5, dated Dec. 11, 2017, 6 pages.
Office Action for European Application No. 15701856.5, mailed Dec. 11, 2017, 6 pages.
Office Action for European Application No. 15726465.6, dated Dec. 10, 2019, 6 pages.
Office Action for Japanese Application No. 2018-036714, dated Jan. 16, 2019, 8 pages.
Office Action for Japanese Application No. 2018-036714, dated Nov. 27, 2019, 5 pages.
Office Action for U.S. Appl. No. 14/400,455, dated Mar. 30, 2017, 10 pages.
Office Action for U.S. Appl. No. 15/201,983, dated Apr. 3, 2019, 16 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Dec. 17, 2018, 17 pages.
Office Action for U.S. Appl. No. 15/201,997, dated Jul. 12, 2018, 12 pages.
Office Action for U.S. Appl. No. 15/334,646, dated Jul. 25, 2017, 19 pages.
Office Action for U.S. Appl. No. 15/334,646, dated Nov. 16, 2017, 26 pages.
Office Action for U.S. Appl. No. 15/341,512, dated Aug. 1, 2019, 19 pages.
Office Action for U.S. Appl. No. 15/341,512, dated Nov. 12, 2019, 18 pages.
Office Action for U.S. Appl. No. 15/341,523, dated Jan. 29, 2019, 10 pages.
Office Action for U.S. Appl. No. 15/341,523, dated Jul. 30, 2019, 8 pages.
Office Action for U.S. Appl. No. 15/354,475, dated May 23, 2019, 7 pages.
Office Action for U.S. Appl. No. 15/484,969, dated Sep. 4, 2019, 12 pages.
Office Action for U.S. Appl. No. 15/499,804, dated Jan. 3, 2018, 20 pages.
Office Action for U.S. Appl. No. 15/672,916, dated Apr. 9, 2019, 31 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/711,266, dated Feb. 23, 2018, 14 pages.
Office Action for U.S. Appl. No. 15/794,717, dated Feb. 1, 2018, 10 pages.
Office Action for U.S. Appl. No. 15/795,062, dated Apr. 9, 2018, 20 pages.
Office Action for U.S. Appl. No. 15/795,062, dated Dec. 19, 2017, 14 pages.
Office Action for U.S. Appl. No. 15/795,062, dated May 3, 2019, 21 pages.
Office Action for U.S. Appl. No. 15/795,075, dated Apr. 10, 2019, 11 pages.
Office Action for U.S. Appl. No. 15/795,075, dated Feb. 6, 2018, 9 pages.
Office Action for U.S. Appl. No. 15/795,075, dated Jul. 16, 2020, 14 pages.
Office Action for U.S. Appl. No. 15/795,075, dated Jul. 31, 2019, 12 pages.
Office Action for U.S. Appl. No. 15/795,075, dated Jun. 15, 2018, 10 pages.
Office Action for U.S. Appl. No. 15/796,255, dated Jan. 10, 2018, 12 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
Office Action for U.S. Appl. No. 15/819,726, dated Jun. 4, 2018, 17 pages.
Office Action for U.S. Appl. No. 15/917,194, dated Apr. 29, 2019, 10 pages.
Office Action for U.S. Appl. No. 15/917,194, dated Dec. 20, 2019, 10 pages.
Office Action for U.S. Appl. No. 15/917,194, dated Jun. 4, 2018, 17 pages.
Office Action for U.S. Appl. No. 15/917,194, dated Oct. 9, 2018, 13 pages.
Office Action for U.S. Appl. No. 15/970,404, dated Apr. 12, 2019, 20 pages.

(56) References Cited

OTHER PUBLICATIONS

Office Action for U.S. Appl. No. 15/970,404, dated Oct. 9, 2018, 21 pages.
Office Action for U.S. Appl. No. 16/181,027, dated Sep. 4, 2019, 12 pages.
Office Action for U.S. Appl. No. 16/240,066, dated May 29, 2019, 7 pages.
Office Action for U.S. Appl. No. 16/375,561, dated Oct. 17, 2019, 15 pages.
Office Action for U.S. Appl. No. 16/405,515, dated Sep. 6, 2019, 9 pages.
Office Action for U.S. Appl. No. 16/416,677, dated Aug. 15, 2019, 8 pages.
Office Action for U.S. Appl. No. 15/201,983, mailed Apr. 3, 2019, 16 pages.
Office Action for U.S. Appl. No. 15/201,997, mailed Aug. 29, 2017, 12 pages.
Office Action for U.S. Appl. No. 15/201,997, mailed Dec. 17, 2018, 17 pages.
Office Action for U.S. Appl. No. 15/201,997, mailed Jul. 12, 2018, 12 pages.
Office Action for U.S. Appl. No. 15/334,646, mailed Jul. 25, 2017, 19 pages.
Office Action for U.S. Appl. No. 15/334,646, mailed Nov. 16, 2017, 26 pages.
Office Action for U.S. Appl. No. 15/341,523, mailed Jul. 30, 2019, 8 pages.
Office Action for U.S. Appl. No. 15/354,475, mailed May 23, 2019, 7 pages.
Office Action for U.S. Appl. No. 15/484,969, mailed Sep. 4, 2019, 12 pages.
Office Action for U.S. Appl. No. 15/499,804, mailed Jan. 3, 2018, 20 pages.
Office Action for U.S. Appl. No. 15/672,916, mailed Apr. 9, 2019, 31 pages.
Office Action for U.S. Appl. No. 15/672,916, mailed Feb. 13, 2018, 16 pages.
Office Action for U.S. Appl. No. 15/672,916, mailed Jul. 20, 2018, 23 pages.
Office Action for U.S. Appl. No. 15/794,717, mailed Feb. 1, 2018, 10 pages.
Office Action for U.S. Appl. No. 15/795,075, mailed Apr. 10, 2019, 11 pages.
Office Action for U.S. Appl. No. 15/795,075, mailed Feb. 6, 2018, 9 pages.
Office Action for U.S. Appl. No. 15/795,075, mailed Jun. 15, 2018, 10 pages.
Office Action for U.S. Appl. No. 15/796,255, mailed Jan. 10, 2018, 12 pages.
Office Action for U.S. Appl. No. 15/796,375, mailed May 30, 2018, 26 pages.
Office Action for U.S. Appl. No. 15/796,375, mailed Nov. 16, 2018, 27 pages.
Office Action for U.S. Appl. No. 15/917,194, mailed Apr. 29, 2019, 10 pages.
Office Action for U.S. Appl. No. 15/917,194, mailed Jun. 4, 2018, 17 pages.
Office Action for U.S. Appl. No. 15/917,194, mailed Oct. 9, 2018, 13 pages.
Office Action for U.S. Appl. No. 15/970,404, mailed Apr. 12, 2019, 20 pages.
Office Action for U.S. Appl. No. 15/970,404, mailed Oct. 9, 2018, 21 pages.
Office Action for U.S. Appl. No. 16/405,515, mailed Sep. 6, 2019, 9 pages.
Office Action for U.S. Appl. No. 16/416,677, mailed Aug. 15, 2019, 8 pages.
Partial European Search Report for European Application No. 18170210.1, dated Feb. 14, 2019, 13 pages.
Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Supplementary European Search Report for European Application No. 15733297.4, dated Aug. 10, 2017, 7 pages.
Supplementary European Search Report for European Application No. 15806855.1, dated Jan. 3, 2018, 8 pages.
Van Driel, V.J.H.M et al., "Low vulnerability of the right phrenic nerve to electroporation ablation," Heart Rhythm, 12:1838-1844 (2015).
Van Driel, V.J.H.M et al., "Pulmonary Vein Stenosis After Catheter Ablation Electroporation Versus Radiofrequency," Circ Arrhythm Electrophysiol., 7(4):734-738 (2014).
Wittkampf, F.H. et al., "Feasibility of Electroporation for the Creation of Pulmonary Vein Ostial Lesions," J Cardiovasc Electrophysiol, 22(3):302-309 (Mar. 2011).
Wittkampf, F.H. et al., "Myocardial Lesion Depth With Circular Electroporation Ablation," Circ. Arrhythm Electrophysiol., 5(3):581-586 (2012).
Office Action for U.S. Appl. No. 18/674,533 mailed Mar. 19, 2025. 20 pages.

\* cited by examiner

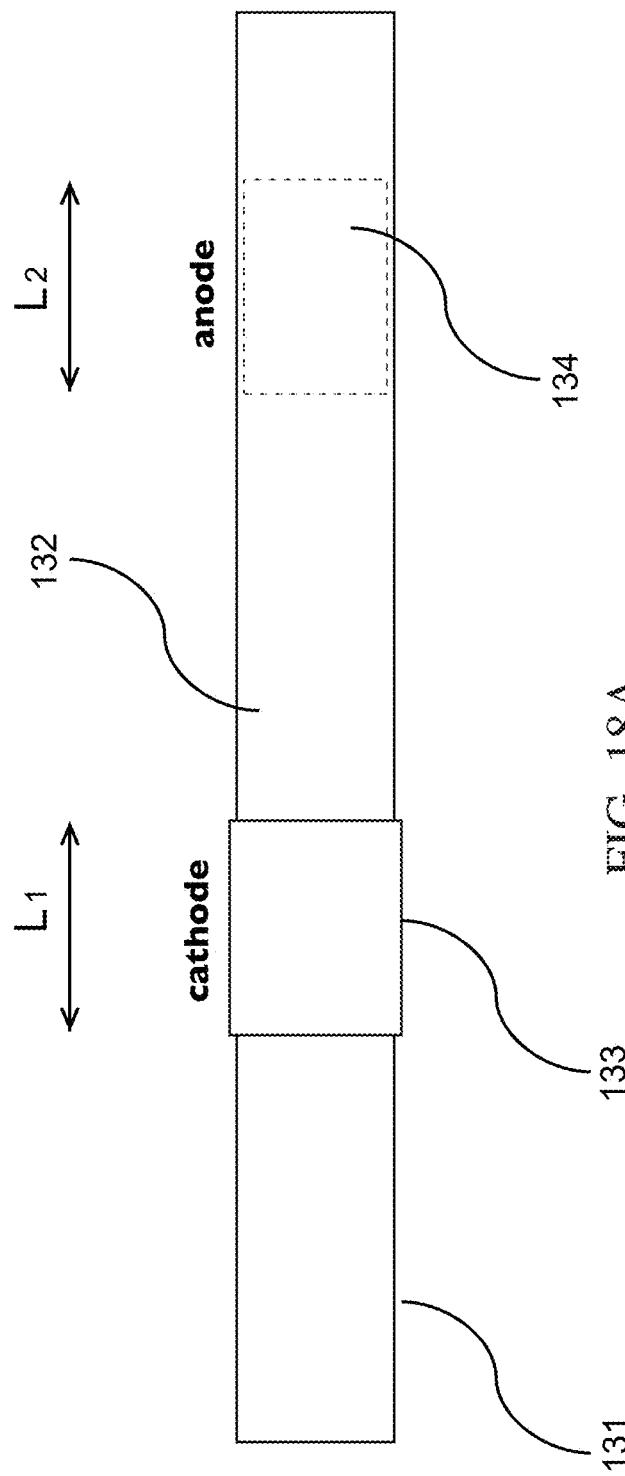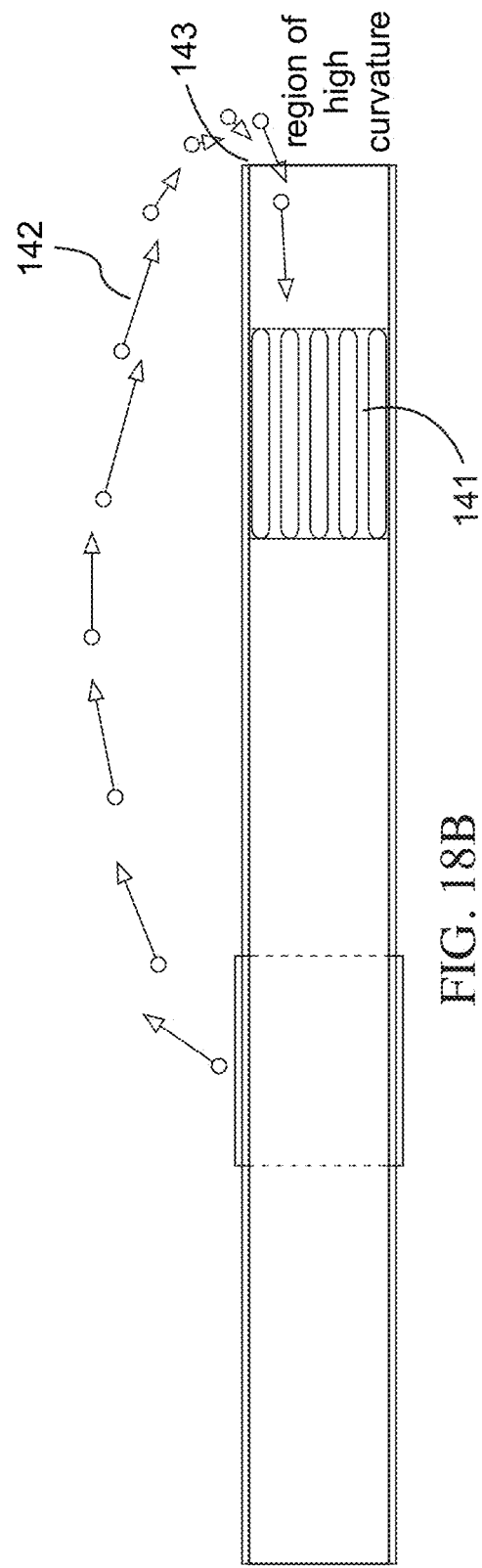
FIG. 18A
FIG. 18B

METHODS AND APPARATUS FOR SELECTIVE TISSUE ABLATION

CROSS-REFERENCE TO RELATED APPLICATIONS

This application is a continuation of U.S. patent application Ser. No. 17/349,299, filed Jun. 16, 2021, which is a continuation of U.S. patent application Ser. No. 15/795,062, filed Oct. 26, 2017, now U.S. Pat. No. 11,259,869, which is a continuation of U.S. patent application Ser. No. 15/341,512, filed Nov. 2, 2016, now Abandoned, which is a continuation of PCT Application No. PCT/US2015/029734, filed May 7, 2015, which claims priority to U.S. Provisional Application Ser. No. 61/996,390, filed May 7, 2014, the entire disclosures of which are incorporated herein by reference.

BACKGROUND

The embodiments described herein relate generally to medical devices for therapeutic electrical energy delivery, and more particularly to systems and methods for delivering electrical energy in the context of ablating tissue rapidly and selectively by the application of suitably timed pulsed voltages that generate irreversible electroporation of cell membranes.

The past two decades have seen advances in the technique of electroporation as it has progressed from the laboratory to clinical applications. Known methods include applying brief, high voltage DC pulses to tissue, thereby generating locally high electric fields, typically in the range of hundreds of Volts/centimeter. The electric fields disrupt cell membranes by generating pores in the cell membrane, which subsequently destroys the cell membrane and the cell. While the precise mechanism of this electrically-driven pore generation (or electroporation) awaits a detailed understanding, it is thought that the application of relatively large electric fields generates instabilities in the phospholipid bilayers in cell membranes, as well as mitochondria, causing the occurrence of a distribution of local gaps or pores in the membrane. If the applied electric field at the membrane exceeds a threshold value, typically dependent on cell size, the electroporation is irreversible and the pores remain open, permitting exchange of material across the membrane and leading to apoptosis or cell death. Subsequently, the surrounding tissue heals in a natural process.

While pulsed DC voltages are known to drive electroporation under the right circumstances, the examples of electroporation applications in medicine and delivery methods described in the prior art do not discuss specificity of how electrodes are selected to accomplish the desired ablation.

There is a need for selective energy delivery for electroporation and its modulation in various tissue types, as well as pulses that permit rapid action and completion of therapy delivery. There is also a need for more effective generation of voltage pulses and control methods, as well as appropriate devices or tools addressing a variety of specific clinical applications. Such more selective and effective electroporation delivery methods can broaden the areas of clinical application of electroporation including therapeutic treatment of a variety of cardiac arrhythmias.

SUMMARY

Catheter systems and methods are disclosed for the selective and rapid application of DC voltage to drive electroporation. In some embodiments, an apparatus includes a voltage pulse generator and an electrode controller. The voltage pulse generator is configured to produce a pulsed voltage waveform. The electrode controller is configured to be operably coupled to the voltage pulse generator and a medical device including a series of electrodes. The electrode controller includes a selection module and a pulse delivery module. The selection module is configured to select a subset of electrodes from the series of electrodes. The selection module is configured identify at least one electrode as an anode and at least one electrode as a cathode. The pulse delivery module is configured to deliver an output signal associated with the pulsed voltage waveform to the subset of electrodes.

BRIEF DESCRIPTION OF THE DRAWINGS

FIG. 18A is a schematic illustration of a distal portion of a catheter having two electrodes functioning as a cathode and an anode according to an embodiment.

FIG. 18B is a schematic illustration of a distal portion of a catheter according to an embodiment having a recessed distal anode electrode, the illustration showing the current flow between electrodes.

DETAILED DESCRIPTION

Figure 1:
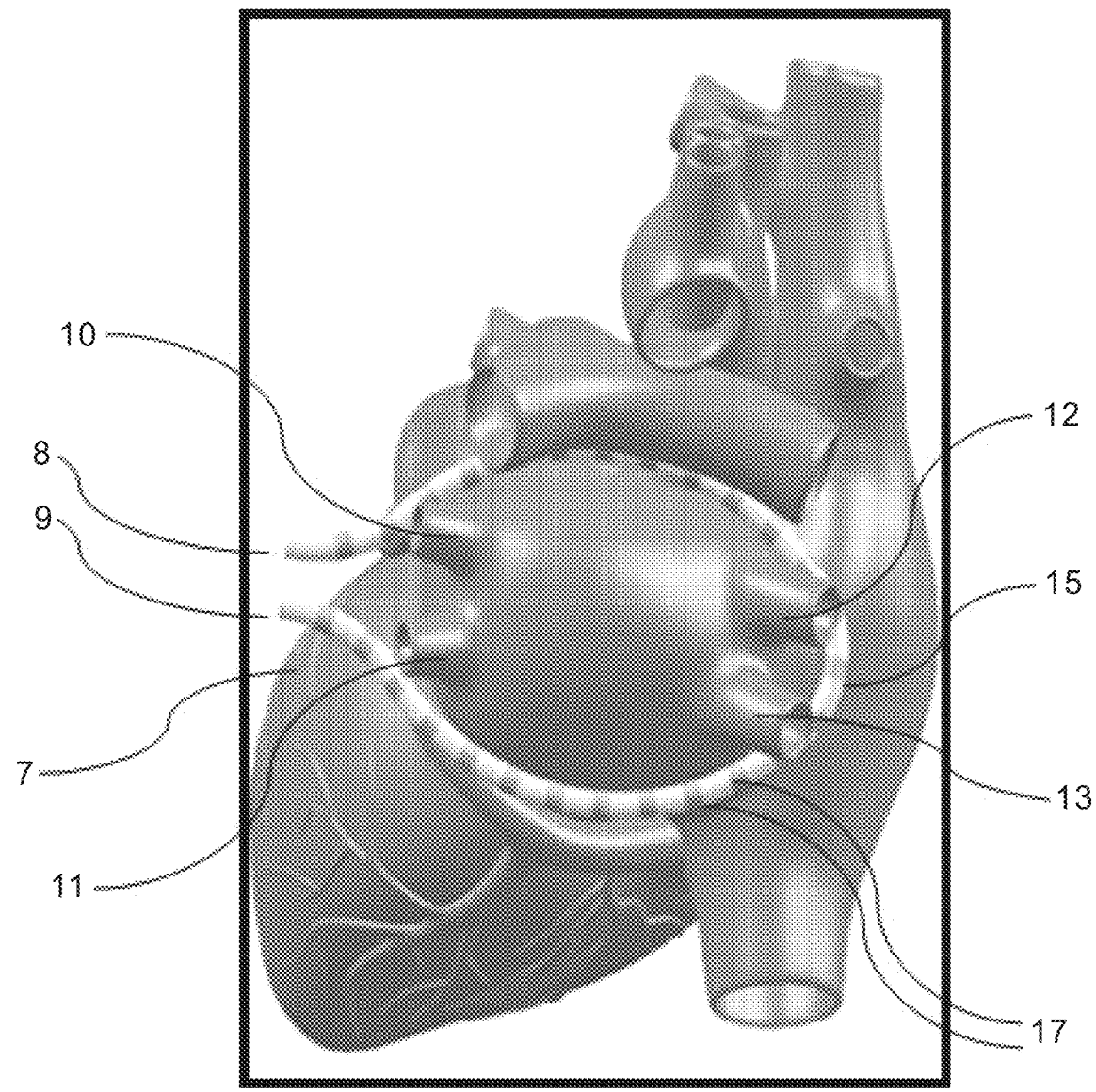
FIG. 1 is a perspective view of a portion of a catheter with multiple electrodes disposed along its shaft and wrapped around the pulmonary veins of the heart such that the portion of the catheter is placed in the epicardial space of the heart.

Systems and methods are disclosed for the selective and rapid application of DC voltage to drive electroporation. In some embodiments, the irreversible electroporation system described herein includes a DC voltage/signal generator and a controller capable of being configured to apply voltages to a selected multiplicity or a subset of electrodes, with anode and cathode subsets being selected independently. The controller is additionally capable of applying control inputs whereby selected pairs of anode-cathode subsets of electrodes can be sequentially updated based on a pre-determined sequence.

In some embodiments, an irreversible electroporation system includes a DC voltage/signal generator and a controller capable of being configured to apply voltages to a selected multiplicity or a subset of electrodes, with independent subset selections for anode and cathode. Further, the controller is capable of applying control inputs whereby selected pairs of anode-cathode subsets of electrodes can be sequentially updated based on a predetermined sequence. The generator can output waveforms that can be selected to generate a sequence of voltage pulses in either monophasic or biphasic forms and with either constant or progressively changing amplitudes. In one embodiment, a DC voltage pulse generation mechanism is disclosed that can use amplified voltage spikes generated by the action of a switch connected to a capacitor bank, resulting in a biphasic, asymmetric micro pulse waveform for cardiac ablation where the first phase provides a brief pre-polarizing pulse that is followed by a finishing pulse in the second phase. Such pre-polarization can result in more effective pulsed voltage electroporation delivery. Methods of control and DC voltage application from a generator capable of selective excitation of sets of electrodes are disclosed. Devices are disclosed for more effective DC voltage application through ionic fluid irrigation and ultrasonic agitation, possibly including insulating balloon constructions to displace electrodes from collateral structures, and for use in intravascular applications. Such devices for generating irreversible electroporation can be utilized in cardiac therapy applications such as ablation to treat Ventricular Tachycardia (VT) as well as in intravascular applications. In some embodiments, the use of temperature to selectively ablate tissue is described, as the threshold of irreversible electroporation is temperature-dependent, utilizing focused kinetic energy to select the predominant tissue type or region it is desired to ablate.

In some embodiments, an apparatus includes a voltage pulse generator and an electrode controller. The voltage pulse generator is configured to produce a pulsed voltage waveform. The electrode controller is configured to be operably coupled to the voltage pulse generator and a medical device including a series of electrodes. The electrode controller is implemented in at least one of a memory or a processor, and includes a selection module and a pulse delivery module. The selection module is configured to select a subset of electrodes from the series of electrodes.

The selection module is configured identify at least one electrode as an anode and at least one electrode as a cathode. The pulse delivery module is configured to deliver an output signal associated with the pulsed voltage waveform to the subset of electrodes.

In some embodiments, an apparatus includes a voltage pulse generator and an electrode controller. The voltage pulse generator is configured to produce a pulsed voltage waveform. The electrode controller is configured to be operably coupled to the voltage pulse generator and a medical device including a series of electrodes. The electrode controller is implemented in at least one of a memory or a processor, and includes a selection module and a pulse delivery module. The selection module is configured to select a set of anode/cathode pairs, each anode/cathode pair including at least one anode electrode and at least one cathode electrode. In some embodiments, for example, the anode/cathode pair can include one anode and multiple cathodes (or vice-versa). The pulse delivery module is configured to deliver an output signal associated with the pulsed voltage waveform to the plurality of anode/cathode pairs according to a sequential pattern.

In some embodiments, a non-transitory processor readable medium storing code representing instructions to be executed by a processor includes code to cause the processor to identify a set of anode/cathode pairs from a set of electrodes of a multi-electrode catheter. The multi-electrode catheter is configured to be disposed about a portion of a heart, and at least one anode/cathode pair includes at least one anode electrode and at least one cathode electrode. The code further includes code to convey a pacing signal to a pacing lead configured to be operatively coupled to the heart. The code further includes code to receive an electrocardiogramal associated with a function of the heart. The code further includes code to deliver a pulsed voltage waveform to the set of anode/cathode pairs according to a sequential pattern.

In some embodiments, a method includes identifying, via a selection module of an electrode controller, a set of anode/cathode pairs from a set of electrodes of a multi-electrode catheter. The multi-electrode catheter is configured to be disposed about a portion of a heart. At least one anode/cathode pair includes at least one anode electrode and at least one cathode electrode. A pacing signal is conveyed to a pacing lead configured to be operatively coupled to the heart. The method further includes receiving, at a feedback module of the electrode controller, an electrocardiogramal associated with a function of the heart. The method further includes delivering, via a pulse delivery module of the electrode controller, a pulsed voltage waveform to the set of anode/cathode pairs according to a sequential pattern.

In some embodiments, an apparatus includes a signal generator for the generation of DC voltage pulses. The signal generator is configured to produce a biphasic waveform having a pre-polarizing pulse followed by a polarizing pulse. The pre-polarizing pulse is generated by utilizing voltage spikes generated from switching on a discharge of a capacitor bank.

In some embodiments, an apparatus includes a catheter shaft, a cathode electrode and an anode electrode. The catheter shaft has an outer side and an inner side. The cathode electrode is coupled to a distal end portion of the catheter shaft such that a cathode surface is exposed on the outer side of the catheter shaft. The anode electrode is coupled to the distal end portion distal relative to the cathode electrode. The anode electrode is recessed within the catheter shaft and coupled to the catheter shaft such that an anode surface is exposed on the inner side of the catheter shaft.

In some embodiments, an apparatus includes a catheter shaft, an inflatable balloon, a first electrode and a second electrode. The catheter shaft has a distal end portion. The inflatable balloon is coupled to the distal end portion. An outer surface of the balloon is an electrical insulator. The first electrode is coupled to a proximal side of the balloon, and the second electrode is coupled to a distal side of the balloon.

In some embodiments, an apparatus includes a catheter shaft having a distal end portion, an expandable basket structure, a first electrode, a second electrode, and a set of spherical electrodes. The expandable basket structure is coupled to the distal end portion of the catheter shaft. The first electrode coupled to a proximal side of the expandable basket structure. The second electrode is coupled to a distal side of the expandable basket structure. The set of spherical electrodes is coupled to a corresponding set of rounded corners of the expandable basket structure.

As used in this specification, the singular forms "a," "an" and "the" include plural referents unless the context clearly dictates otherwise. Thus, for example, the term "a member" is intended to mean a single member or a combination of members, "a material" is intended to mean one or more materials, "a processor" is intended to mean a single processor or multiple processors; and "memory" is intended to mean one or more memories, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100.

As shown in FIG. 1, in some embodiments a Pulmonary Vein isolation (PV isolation) ablation catheter device 15 with a multiplicity of electrodes (indicated by dark bands such as those marked as 17) disposed along its mid-section is wrapped in the epicardial space around the pulmonary veins 10, 11, 12 and 13 of a heart 7 in a subject or patient anatomy, with the ends 8 and 9 of the mid-section extending out and away to eventually emerge from the patient's chest. The ablation catheter 15 and any of the catheters described herein can be similar to the ablation catheters described in PCT Publication No. WO2014/025394, entitled "Catheters, Catheter Systems, and Methods for Puncturing Through a Tissue Structure," filed on Mar. 14, 2013 ("the '394 PCT Application), which is incorporated herein by reference in its entirety. The ablation catheter 15 can be disposed about the pulmonary veins 10, 11, 12 and 13 using any suitable procedure and apparatus. For example, in some embodiments, the ablation catheter 15 can be disposed about the pulmonary veins 10, 11, 12 and 13 and/or the heart 7 using a puncturing apparatus disposed via a subxiphoid pericardial access location and a guidewire-based delivery method as described in the '394 PCT Application. After the ends 8 and 9 of the mid-section extend and emerge out of the patient chest they can be cinched together to effectively hold the catheter in place or position.

A DC voltage for electroporation can be applied to subsets of electrodes identified as anode and cathode, respectively, on approximately opposite sides of the closed contour defined by the shape of the catheter 15 around the pulmonary veins. The DC voltage is applied in brief pulses sufficient to cause irreversible electroporation. In any of the systems and methods described herein, the pulse or waveform can be in the range of 0.5 kV to 10 kV and more preferably in the range 1 kV to 2.5 kV, so that a threshold electric field value of around 200 Volts/cm is effectively achieved in the cardiac tissue to be ablated. In some embodiments, the marked electrodes can be automatically identified, or manually identified by suitable marking, on an X-ray or fluoroscopic image obtained at an appropriate angulation that permits identification of the geometric distance between anode and cathode electrodes, or their respective centroids. In one embodiment, the DC voltage generator setting for irreversible electroporation is then automatically identified by the electroporation system based on this distance measure. In an alternate embodiment, the DC voltage value is selected directly by a user from a suitable dial, slider, touch screen, or any other user interface. The DC voltage pulse results in a current flowing between the anode and cathode electrodes on opposite sides of the contour defined by the catheter shape, with said current flowing through the cardiac wall tissue and through the intervening blood in the cardiac chamber, with the current entering the cardiac tissue from the anode and returning back through the cathode electrodes. The forward and return current paths (leads) are both inside the catheter. Areas of cardiac wall tissue where the electric field is sufficiently large for irreversible electroporation are ablated during the DC voltage pulse application. The number of electrodes on the PV isolation ablation catheter can be in the range between 8 and 50, and more preferably in the range between 15 and 40.

Figure 2A:
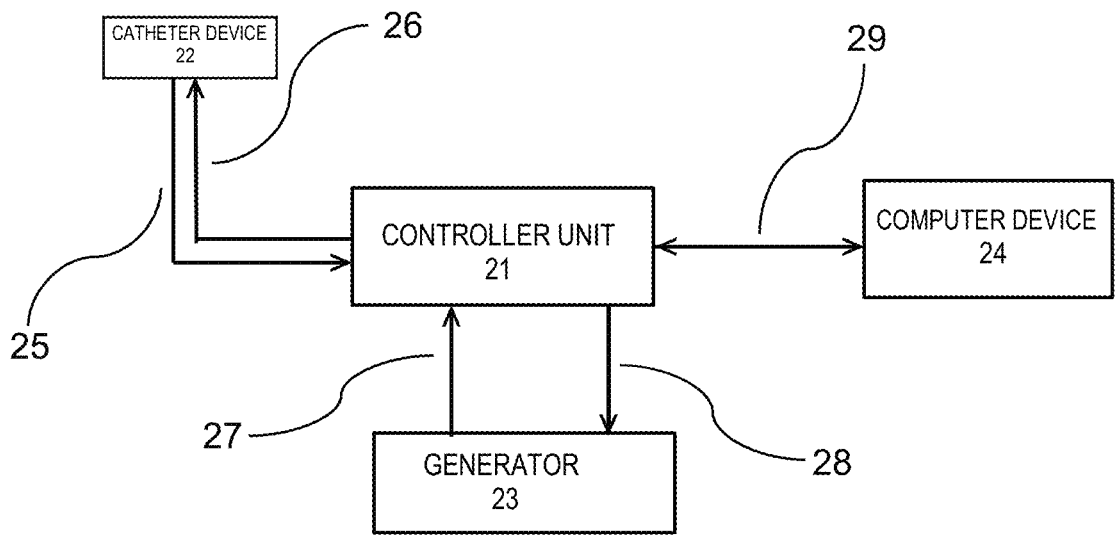
FIG. 2A is a schematic illustration of an irreversible electroporation system that includes a DC voltage/signal generator, a controller capable of being configured to apply voltages to selected subsets of electrodes with independent subset selections for anode and cathode.

A schematic diagram of the electroporation system according to an embodiment is shown in FIG. 2A. The system includes a DC voltage/signal generator 23 that is driven by a controller unit 21 that interfaces with a computer device 24 by means of a two-way communication link 29. The controller can perform channel selection and routing functions for applying DC voltages to appropriate electrodes that have been selected by a user or by the computer 24, and apply the voltages via a multiplicity of leads (shown collectively as 26) to a catheter device 22. The catheter device can be any of the catheters shown and described herein or in the '394 PCT Application. Some leads from the controller 21 could also carry pacing signals to drive pacing of the heart through a separate pacing device (not shown). The catheter device can also send back information such as ECG (electrocardiogramaings or data from other sensors back to the controller 21 as indicated by the data stream 25, possibly on separate leads. While the DC voltage generator 23 sends a DC voltage to the controller 21 through leads 27, the voltage generator is driven by control and timing inputs 28 from the controller unit 21.

Figure 2B:
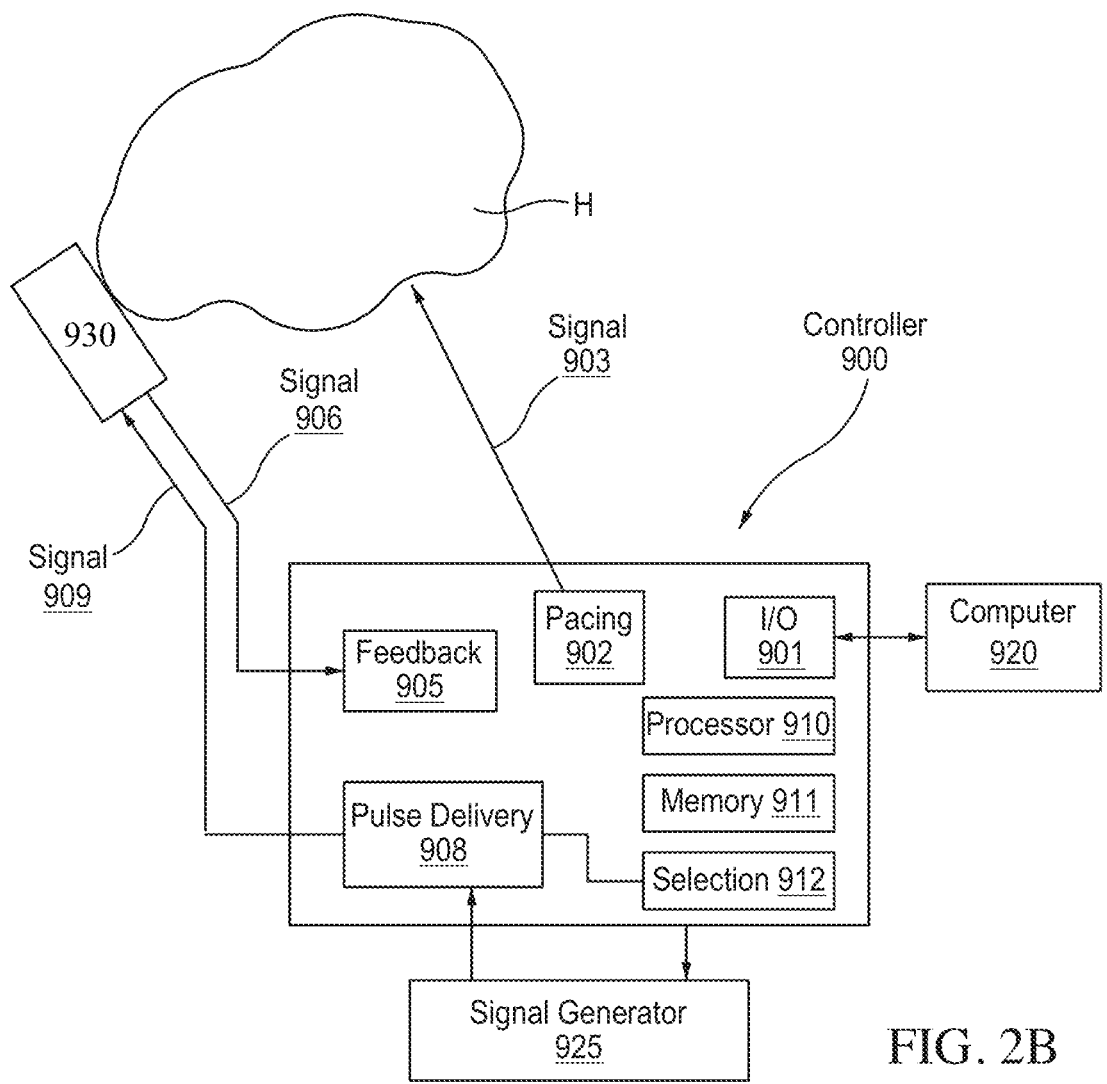
FIG. 2B is a schematic illustration of an irreversible electroporation system that includes a DC voltage/signal generator and a controller according to an embodiment.

In some embodiments, the electrode controller can include one or more modules and can automatically perform channel selection (e.g., identification of a subset of electrodes to which the voltage pulses will be applied), identification of the desired anode/cathode pairs, or the like. For example, FIG. 2B shows an electroporation system according to an embodiment that includes an electrode controller 900 and a signal generator 925. The electrode controller 900 is coupled to a computer 920 or other input/output device, and is configured to be operable coupled to a medical device 930. The medical device 930 can be one or more multi-electrode catheters, of the types shown and described herein. Further the medical device 930 can be coupled to, disposed about and/or in contact with a target tissue, such as the heart H. In this manner, as described herein, the electroporation system, including the electrode controller 900 and the signal generator 925, can deliver voltage pulses to the target tissue for therapeutic purposes.

The controller 900 can include a memory 911, a processor 910, and an input/output module (or interface) 901. The controller 900 can also include a pacing module 902, a feedback module 905, a pulse delivery module 908, and a selection module 912. The electrode controller 900 is coupled to a computer 920 or other input/output device via the input/output module (or interface) 901.

The processor 910 can be any processor configured to, for example, write data into and read data from the memory 911, and execute the instructions and/or methods stored within the memory 911. Furthermore, the processor 910 can be configured to control operation of the other modules within the controller (e.g., the pacing module 902, the feedback module 905, the pulse delivery module 908, and the selection module 912). Specifically, the processor can receive a signal including user input, impedance, heart function or the like information and determine a set of electrodes to which voltage pulses should be applied, the desired timing and sequence of the voltage pulses and the like. In other embodiments, the processor 910 can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device 910 can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pacing module 902, the feedback module 905, the pulse delivery module 908, and the selection module 912) can be implemented by the processor 910 and/or stored within the memory 910.

As shown, the electrode controller 900 operably coupled to the signal generator 925. The signal generator includes circuitry, components and/or code to produce a series of DC voltage pulses for delivery to electrodes included within the medical device 930. For example, in some embodiments, the signal generator 925 can be configured to produce a biphasic waveform having a pre-polarizing pulse followed by a polarizing pulse. The signal generator 925 can be any suitable signal generator of the types shown and described herein.

The pulse delivery module 908 of the electrode controller 900 includes circuitry, components and/or code to deliver an output signal associated with the pulsed voltage waveform produced by the signal generator 925. This signal (shown as signal 909) can be any signal of the types shown and described herein, and can be of a type and/or have characteristics to be therapeutically effective. In some embodiments, the pulse delivery module 908 receives input from the selection module 912, and can therefore send the signal 909 to the appropriate subset of electrodes, as described herein.

The selection module 912 includes circuitry, components and/or code to select a subset of electrodes from the electrodes included within the medical device 930, as described herein. In some embodiments, the selection module 912 is configured identify at least one electrode from the subset of electrodes as an anode and at least one electrode from the subset of electrodes as a cathode. In some embodiments, the selection module 912 is configured to select a subset of electrodes from more than one medical device 930, as described herein.

In some embodiments, the selection module 912 can select the subset of electrodes based on input received from the user via the input/output module 901. For example, in some embodiments, the user can use visualization techniques or other methods to identify the desired electrodes, and can manually enter those electrodes, as described herein.

In other embodiments, the selection module 912 is configured to select the subset of electrodes based on a predetermined schedule of the set of electrodes. For example, in some embodiments, the electrode controller 900 can be configured accommodate different medical devices 930 having different numbers and/or types of electrodes. In such embodiments, the selection module 912 can retrieve a pre-determined schedule of electrodes to which a series of voltage pulses can be applied, based on the specific type of medical device 930.

In yet other embodiments, the selection module 912 is configured to select the subset of electrodes automatically based on at least one of an impedance associated with the subset of electrodes, a distance between the first electrode and the second electrode, and a characteristic associated with a target tissue. For example, in some embodiments, the electrode controller 900 includes the feedback module 905 that can receive feedback from the medical device 930 (as identified by the signal 906). The feedback module 905 includes circuitry, components and/or code to determine an impedance between various electrodes (as described herein). Thus, in such embodiments, the selection module 912 can select the subset of electrodes automatically based the impedance.

In some embodiments, the electrode controller 900 optionally includes the pacing module 902. The pacing module 902 includes circuitry, components and/or code to produce a pacing signal (identified as signal 903) that can be delivered to the target tissue (or heart) via a pacing lead. As described herein, the pacing module 902 can facilitate any suitable "mode" of operation desired, such as a standard pacing, an overdrive pacing option (for pacing at a faster-than-normal heart rate), an external trigger option (for pacing from an externally generated trigger), and a diagnostic pacing option.

Figure 3:
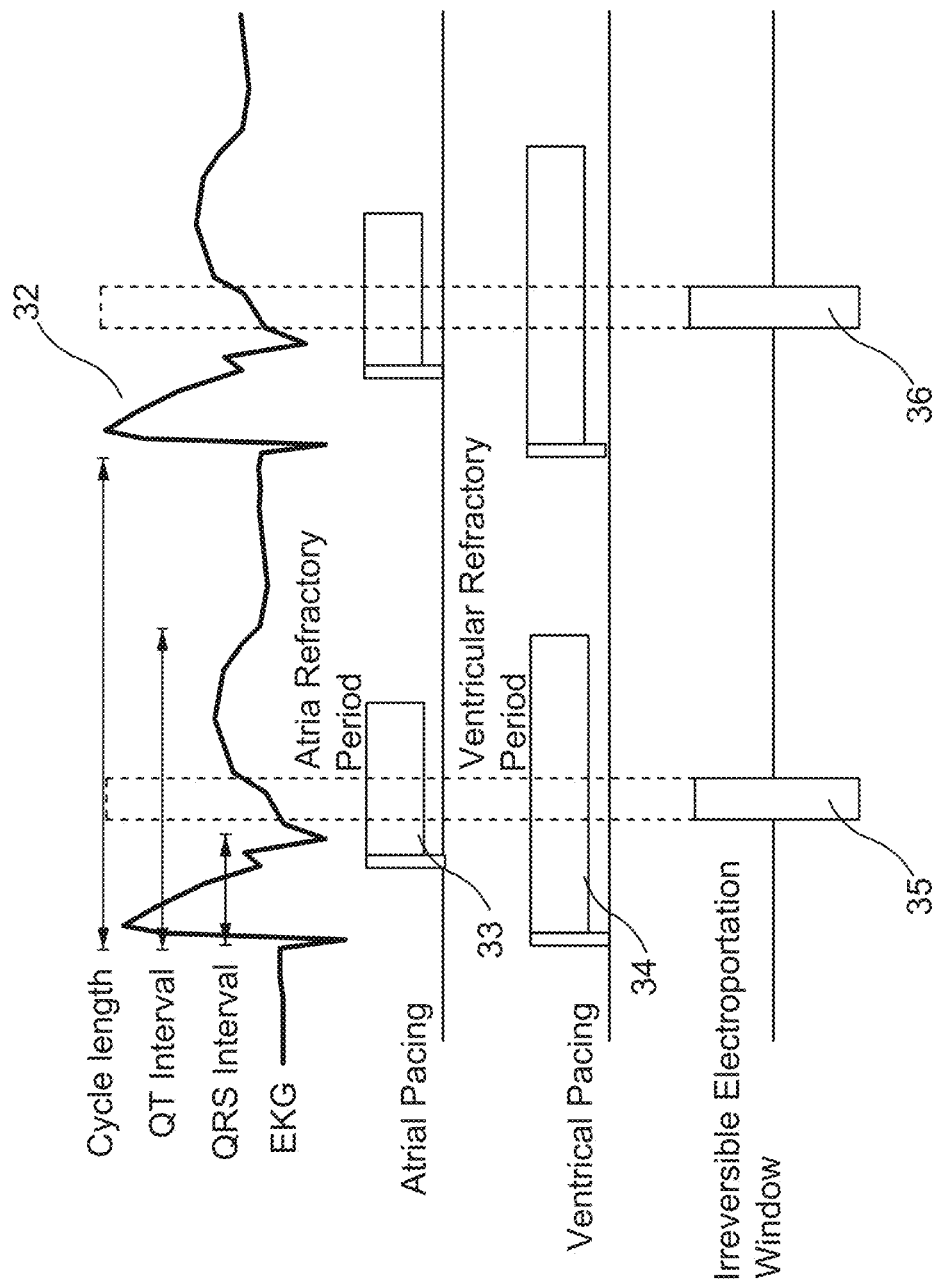
FIG. 3 is an illustration of an ECG waveform showing the refractory periods during atrial and ventricular pacing, and the time windows for irreversible electroporation ablation.
Figure 4:
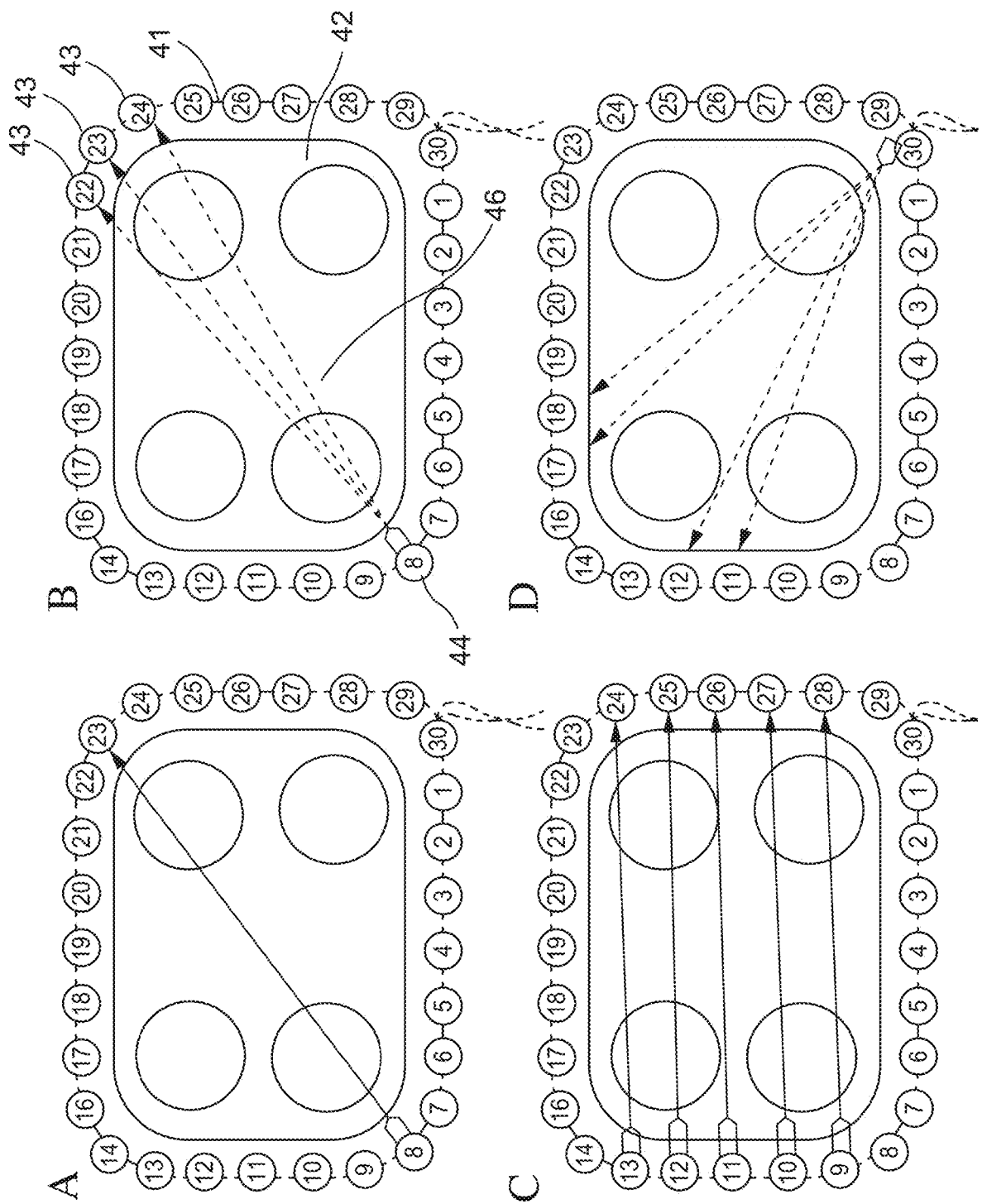
FIG. 4 is a schematic illustration of a user interface according to an embodiment showing various configurations for subsets of electrodes on the catheter to be identified as anodes or cathodes, and the ablation vectors therebetween.

As shown in FIG. 3, given atrial or ventricular pacing inputs to the heart (e.g., from the pacing module 902 of the electrode controller 900), the resulting ECG waveform 32 has appropriate respective refractory time intervals 33 and 34 respectively, during which there are suitable time windows for application of irreversible electroporation as indicated by 35 and 36. The application of cardiac pacing results in a periodic, well-controlled sequence of electroporation time windows. Typically, this time window is of the order of hundreds of microseconds to about a millisecond or more. During this window, multiple DC voltage pulses can be applied to ensure that sufficient tissue ablation has occurred. The user can repeat the delivery of irreversible electroporation over several successive cardiac cycles for further confidence. Thus, in some embodiments, a feedback module (e.g., feedback module 905) can receive the electrocardiogramal, and a pulse delivery module (e.g., pulse delivery module 908) can deliver the output signal to the subset of electrodes during a time window associated with at least one a pacing signal or the electrocardiogramaignal.

In some embodiments, the ablation controller and signal generator can be mounted on a rolling trolley, and the user can control the device using a touchscreen interface that is in the sterile field. Referring to FIG. 2B, in such embodiments, the computer 920 can be a touchscreen device. The touchscreen can be for example an LCD touchscreen in a plastic housing mountable to a standard medical rail or post and can be used to select the electrodes for ablation and to ready the device to fire. The interface can for example be covered with a clear sterile plastic drape. The operator can select the number of electrodes involved in an automated sequence. The touch screen graphically shows the catheters that are attached to the controller. In one embodiment the operator can select electrodes from the touchscreen with appropriate graphical buttons. The operator can also select the pacing stimulus protocol (either internally generated or externally triggered) from the interface. Once pacing is enabled, and the ablation sequence is selected, the operator can initiate or verify pacing. Once the operator verifies that the heart is being paced, the ablation sequence can be initiated by holding down a hand-held trigger button that is in the sterile field. The hand-held trigger button can be illuminated red to indicate that the device is "armed" and ready to ablate. The trigger button can be compatible for use in a sterile field and when attached to the controller can be illuminated a different color, for example white. When the device is firing, the trigger button flashes in sequence with the pulse delivery in a specific color such as red. The waveform of each delivered pulse is displayed on the touchscreen interface. A graphic representation of the pre and post impedance between electrodes involved in the sequence can also be shown on the interface, and this data can be exported for file storage.

In some embodiments, an impedance map can be generated based on voltage and current recordings across anode-cathode pairs or sets of electrodes, and an appropriate set of electrodes that are best suited for ablation delivery in a given region can be selected based on the impedance map or measurements, either manually by a user or automatically by the system. Such an impedance map can be produced, for example, by the feedback module 905, or any other suitable portion of the electrode controller 900. For example, if the impedance across an anode/cathode combination of electrodes is a relatively low value (for example, less than 25 Ohms), at a given voltage the said combination would result in relatively large currents in the tissue and power dissipation in tissue. In such circumstances, this electrode combination would then be ruled out (e.g., via the selection module 912) for ablation due to safety considerations, and alternate electrode combinations would be sought by the user. In a preferred embodiment, a pre-determined range of impedance values, for example 30 Ohms to 300 Ohms, could be used as an allowed impedance range within which it is deemed safe to ablate. Thus, in some embodiments, an electrode controller can automatically determine a subset of electrodes to which voltage pulses should be applied.

The waveforms for the various electrodes can be displayed and recorded on the case monitor and simultaneously outputted to a standard connection for any electrophysiology (EP) data acquisition system. With the high voltages involved with the device, the outputs to the EP data acquisition system needs to be protected from voltage and/or current surges. The waveforms acquired internally can be used to autonomously calculate impedances between each electrode pair. The waveform amplitude, period, duty cycle, and delay can all be modified, for example via a suitable Ethernet connection. Pacing for the heart is controlled by the device and outputted to the pacing leads and a protected pacing circuit output for monitoring by a lab.

While a touchscreen interface is one preferred embodiment, other user interfaces can be used to control the system such as a graphical display on a laptop or monitor display controlled by a standard computer mouse or joystick. FIG.

4 shows a schematic rendering of a portion of the user interface of the electroporation system. The four windows A, B, C and D shown in the FIG. represent four different choices of electrode subsets for anode and cathode selection. The PV isolation ablation catheter is represented by a string of numbered electrodes as indicated by 41, wrapped around the area 42 of the pulmonary veins represented by the enclosed region in this schematic diagram. Referring to B in the FIG., the dashed-line vectors 46 represent approximate current vectors, with their tips at the cathodes and tails or bases at the anodes; in this FIG., the three electrodes marked 43 are cathodes, and the single electrode marked 44 is the anode. The windows A, C and D in this FIG. show other choices of cathode and anode electrode subsets, in each case with accompanying approximate current density vectors shown by dashed arrows. It is clear from the FIG. that the user can select various subsets of electrodes as cathode or anode, depending on the region to be ablated along the length of the PV isolation catheter. In one embodiment, the user can make one selection of cathode and anode subsets, and the system can take this selection as input to generate an ablation sequence that moves around the ring or contour defined by the shape of the PV isolation catheter, for example moving clockwise at each step with a one-electrode displacement. In this manner, the pair of cathode and anode electrode subsets can be sequentially updated for ablation purposes, so that if there are N electrodes, after N updates the entire contour has been updated such that the tips of the current arrows shown as 46 have swept once around the contour completely.

Figure 5:
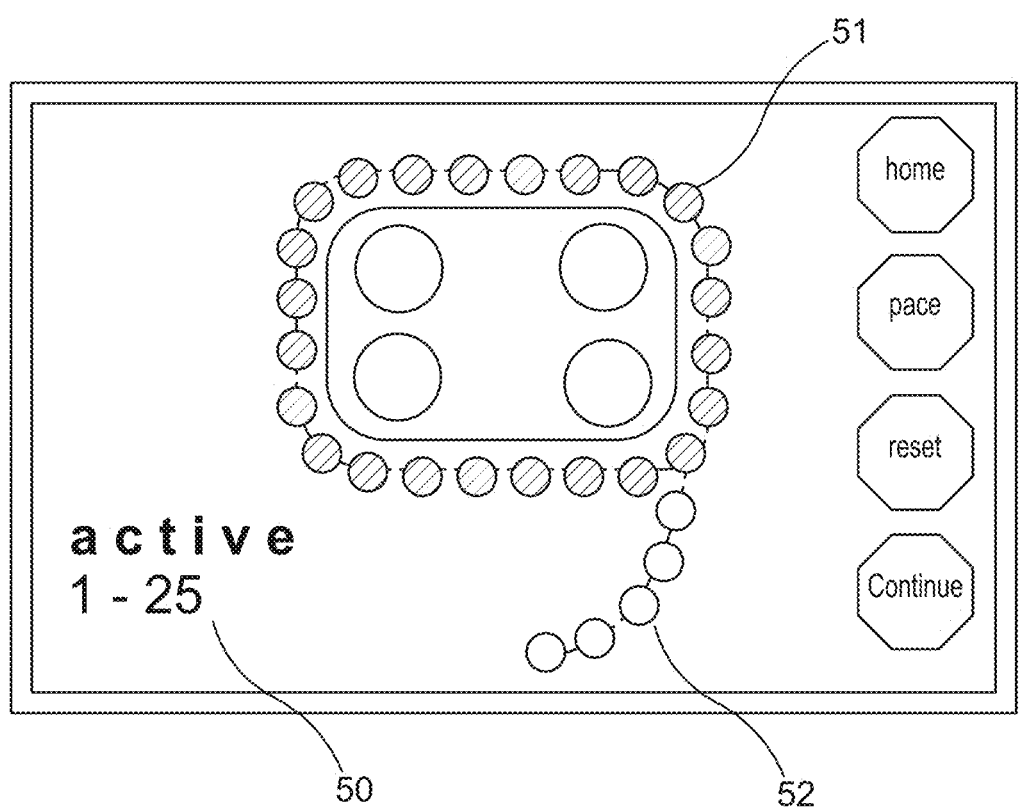
FIG. 5 is a schematic illustration of a user interface according to an embodiment, indicating the electrodes that are active and wrapped around the pulmonary veins of a patient anatomy, and that can be actively available for selection in bipolar ablation.

In some cases, the portion of the PV isolation catheter with electrodes may be longer than needed to wrap around a given patient's pulmonary veins; in this event, a smaller number of electrodes suffices to wrap around the contour of the pulmonary veins. These define the number of "active" electrodes to be used in the ablation process. In the specific example shown in FIG. 5 for a 30-electrode PV isolation catheter, the set of electrodes wrapped around the pulmonary veins, represented by 51, are the electrodes that would be used in the ablation process, and are called out by the label 50 as the set of active electrodes, while the remaining five electrodes represented by 52 are not used in the ablation process as they are not located in suitable positions.

Figure 6:
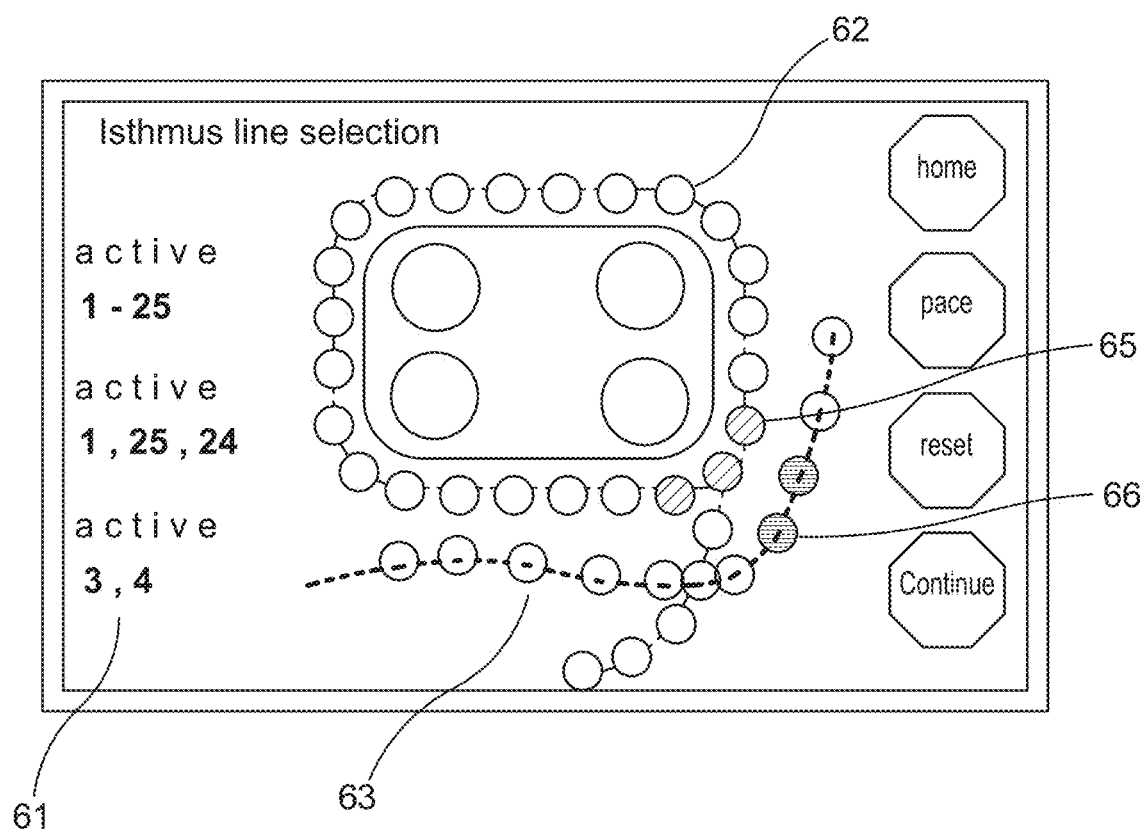
FIG. 6 is a schematic illustration of a user interface according to an embodiment that illustrates a method of ablating along a cardiac isthmus line using two catheters, one of which is wrapped around the pulmonary veins.

In one embodiment of the electroporation system disclosed herein, multiple catheters could be used for ablation, with anode and cathode subsets respectively chosen to lie on different catheters. In one exemplary use of such multi-device electroporation, two catheters are connected to the controller unit of the electroporation system. In some instances of ablation procedures for the treatment of Atrial Fibrillation (AF), in addition to isolating the pulmonary veins, it is also useful to generate an ablation line that separates or isolates regions around the mitral valve. Such a line is often termed a "Mitral Isthmus Line," and is a line running from an Inferior aspect of the PV isolation contour to the outer edge of the mitral valve in the left atrium. In some embodiments, a method of use of the systems described herein includes inserting a coronary sinus catheter with multiple electrodes into the coronary sinus. As shown in FIG. 6, electrodes marked as 66 on the coronary sinus catheter 63, and electrodes marked as 65 on the PV isolation catheter 62, are further selected as active subsets of electrodes for ablation, as indicated in the indication window 61 for the anode and cathode subsets. Thus in effect the electrodes of the coronary sinus catheter 63 are utilized to define the mitral isthmus line, and irreversible electroporation ablation can be effectively performed on the left atrial wall to generate a mitral isthmus ablation line.

In a some embodiments, the system (any of the generators and controllers described herein) can deliver rectangular-wave pulses with a peak maximum voltage of about 5 kV into a load with an impedance in the range of 30 Ohm to 3000 Ohm for a maximum duration of 200 μs, with a 100 μs maximum duration being still more preferred. Pulses can be delivered in a multiplexed and synchronized manner to a multi-electrode catheter inside the body with a duty cycle of up to 50% (for short bursts). The pulses can generally be delivered in bursts, such as for example a sequence of between 2 and 10 pulses interrupted by pauses of between 1 ms and 1000 ms. The multiplexer controller is capable of running an automated sequence to deliver the impulses/impulse trains (from the DC voltage signal/impulse generator) to the tissue target within the body. The controller system is capable of switching between subsets/nodes of electrodes located on the single use catheter or catheters (around or within the heart). Further, the controller can measure voltage and current and tabulate impedances in each electrode configuration (for display, planning, and internal diagnostic analysis). It can also generate two channels of cardiac pacing stimulus output, and is capable of synchronizing impulse delivery with the internally generated cardiac pacing and/or an external trigger signal. In one embodiment, it can provide sensing output/connection for access to bio potentials emanating from each electrode connected to the system (with connectivity characteristics being compatible with standard electrophysiological laboratory data acquisition equipment).

In a some embodiments, the controller (e.g., the controller 900) can automatically "recognize" the single-use disposable catheter when it is connected to the controller output (prompting internal diagnostics and user interface configuration options). The controller can have at least two unique output connector ports to accommodate up to at least two catheters at once (for example, one 30-electrode socket and one 10-electrode socket; a 2-pole catheter would connect to the 10-pole socket). The controller device can function as long as at least one recognized catheter is attached to it. In a preferred embodiment, the controller can have several sequence configurations that provide the operator with at least some variety of programming options. In one configuration, the controller can switch electrode configurations of a bipolar set of electrodes (cathode and anode) sequentially in a clockwise manner (for example, starting at step n, in the next step of the algorithm, cathode n+1 and anode n+1 are automatically selected, timed to the synchronizing trigger). With the 30-pole catheter the electrodes are arranged in a quasi-circumference around the target. Thus in the first sequence, pulse delivery occurs so that the vector of current density changes as the automated sequencing of the controller switches "on" and "off" between different electrodes surrounding the tissue target sequence. The current density vectors generally cross the target tissue but in some configurations the current density could be approximately tangential to the target. In a second sequence configuration, the impulses are delivered to user-selected electrode subsets of catheters that are connected to the device (the vector of current density does not change with each synchronized delivery). A third sequence configuration example is a default bipolar pulse sequence for the simplest 2-pole catheter. The user can also configure the controller to deliver up to 2 channels of pacing stimulus to electrodes connected to the device output. The user can control the application of DC voltage with a single handheld switch. A sterile catheter or catheters can be connected to the voltage output of the generator via a connector cable that can be delivered to the sterile field. In one embodiment, the user activates the device with a touch screen interface (that can be protected with a single-use sterile transparent disposable cover commonly available in the catheter lab setting). The generator can remain in a standby mode until the user is ready to apply pulses at which point the user/assistant can put the generator into a ready mode via the touchscreen interface. Subsequently the user can select the sequence, the active electrodes, and the cardiac pacing parameters.

Once the catheter has been advanced to or around the cardiac target, the user can initiate electrically pacing the heart (using a pacing stimulus generated by the ablation controller or an external source synchronized to the ablation system). The operator verifies that the heart is being paced and uses the hand-held trigger button to apply the synchronized bursts of high voltage pulses. The system can continue delivering the burst pulse train with each cardiac cycle as long as the operator is holding down a suitable "fire" button or switch. During the application of the pulses, the generator output is synchronized with the heart rhythm so that short bursts are delivered at a pre-specified interval from the paced stimulus. When the train of pulses is complete, the pacing continues until the operator discontinues pacing.

Figure 7:
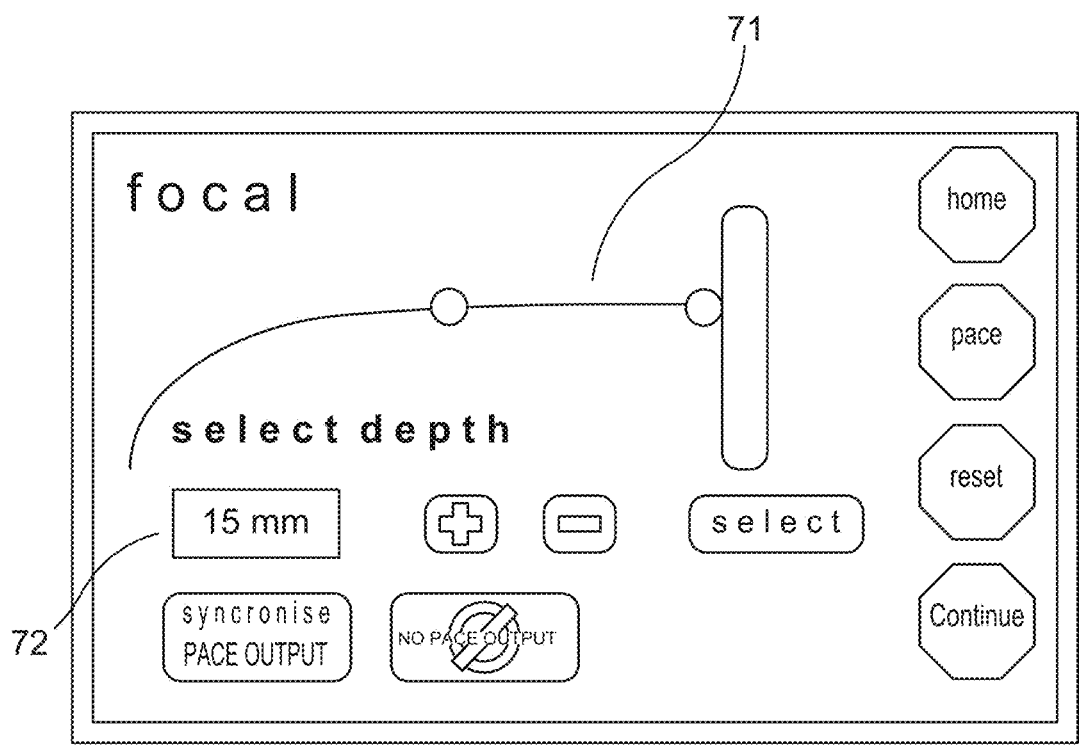
FIG. 7 is a schematic illustration of a user interface according to an embodiment that illustrates a method of focal ablation, wherein nearby electrodes on the same catheter are used for bipolar ablation with irreversible electroporation to ablate a region of contacting tissue at the distal catheter end, and showing a depth selection button that can be used to selectively adjust an ablation parameter.

FIG. 7 shows a portion of a graphical user interface according to an embodiment for focal ablation with a bipolar or 2-electrode catheter. In some embodiments, the graphical user interface can be a touchscreen interface. A graphical icon 71 for a bipolar catheter is shown along with a depth selection button 72 for selecting a desired ablation depth. In one embodiment of the system, based on the latter depth setting, the system can select an appropriate voltage value to apply in order to ensure that an electric field sufficient to cause irreversible electroporation is applied up to the desired depth.

Figure 8:
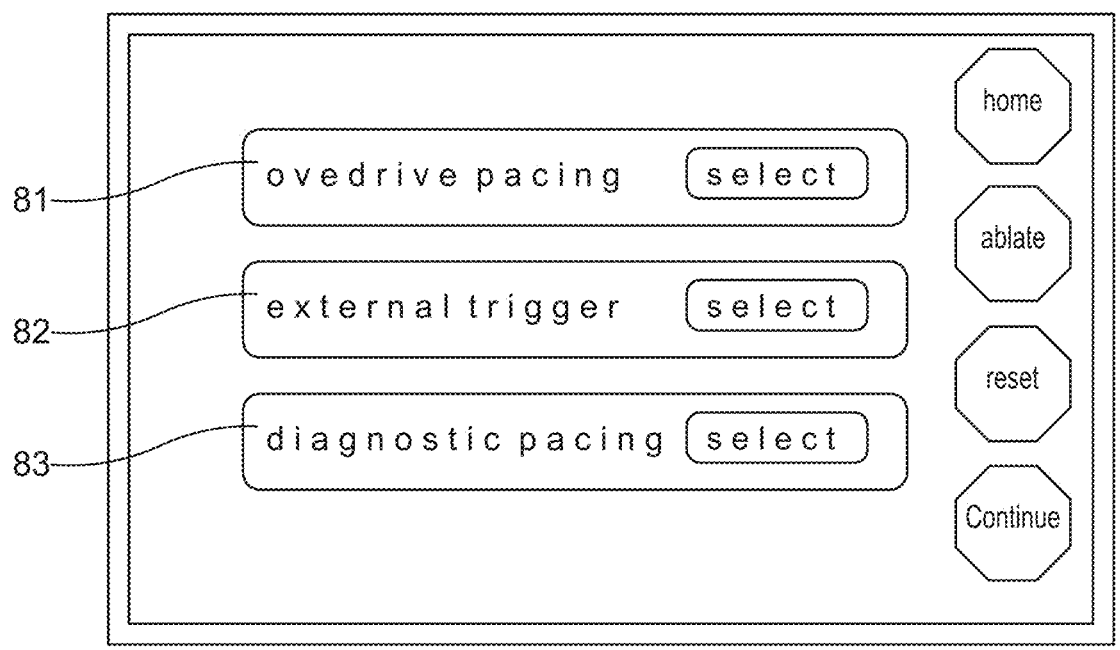
FIG. 8 is a schematic illustration according to an embodiment, showing a graphic window for selection of type of pacing to be used for electroporation therapy delivery.

In some embodiments, a pacing selection interface on a portion of the user interface of the electroporation system is shown in FIG. 8. The pacing selection interface has various options such as an overdrive pacing option 81 for pacing at a faster-than-normal heart rate, an external trigger option 82 for pacing from an externally generated trigger, and a diagnostic pacing option 83. By clicking the "Select" button for a given option, that option is selected.

Figure 9:
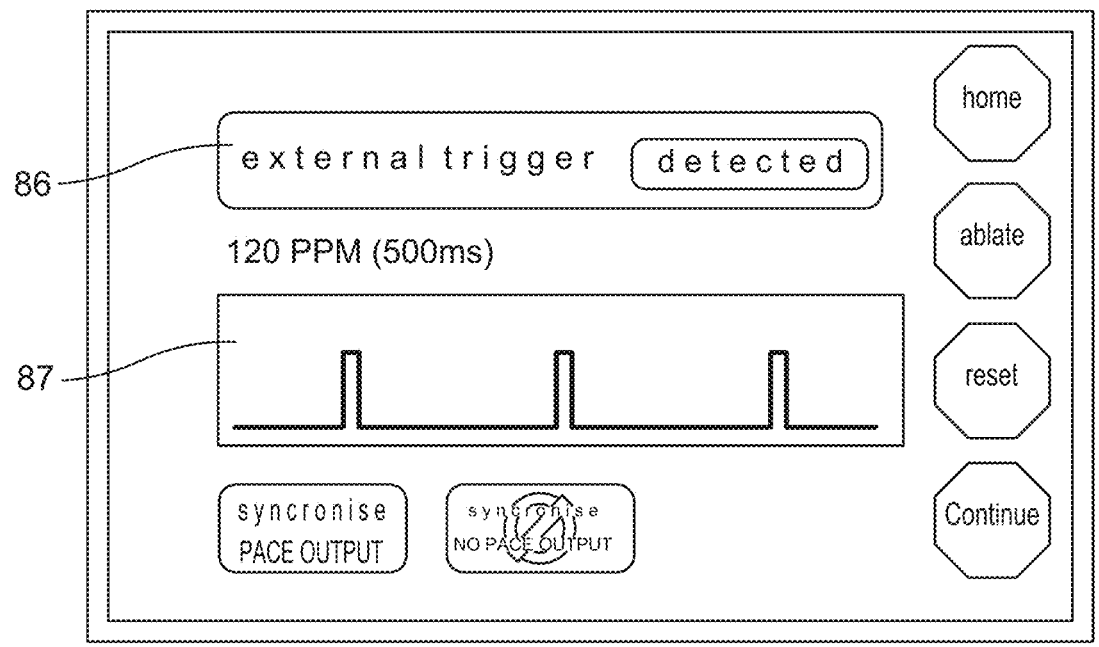
FIG. 9 is a schematic illustration of a user interface according to an embodiment, showing a graphic window with parameters associated with a selected pacing type.

As an example of a pacing option selected, FIG. 9 shows a portion the user interface of the electroporation system with pacing from an external trigger selected for the pacing option. The selected option 86 is displayed along with the pacing characteristics and waveform 87 for the user to visualize.

Figure 10:
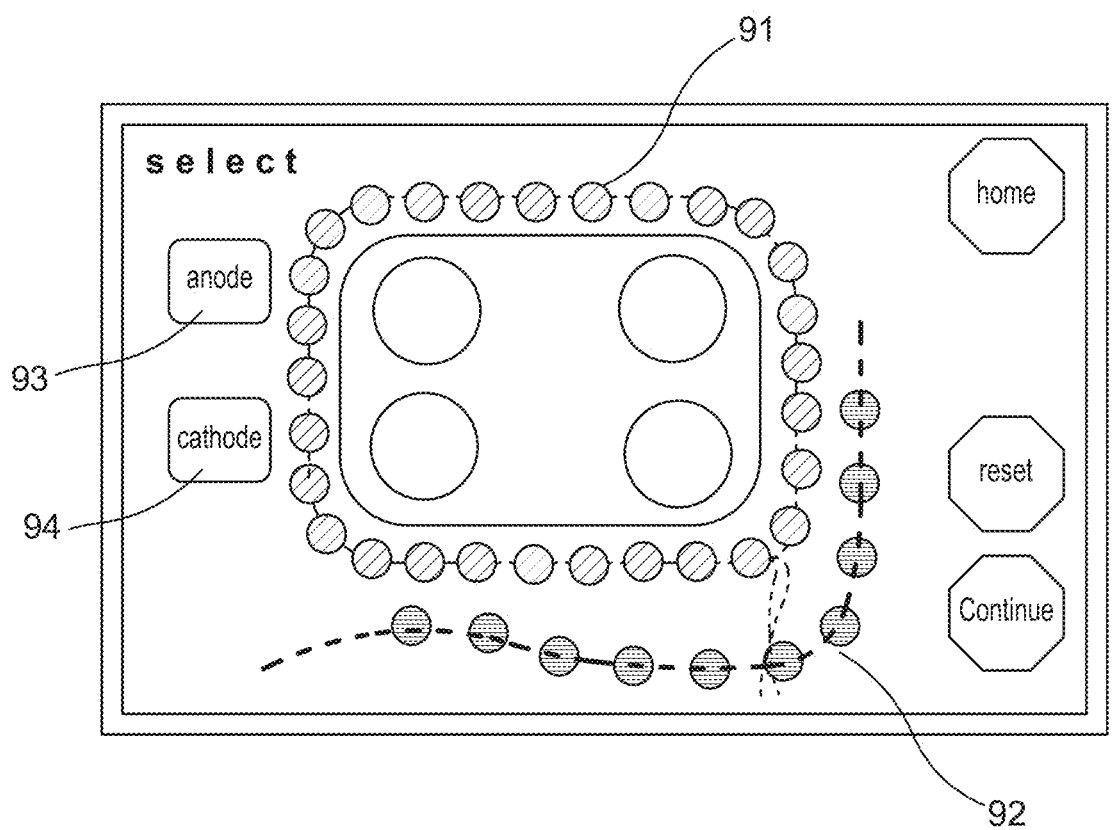
FIG. 10 is a schematic illustration of a user interface that illustrates a method of selecting anode electrode subsets and cathode electrode subsets on two different catheters according to an embodiment.
Figure 11:
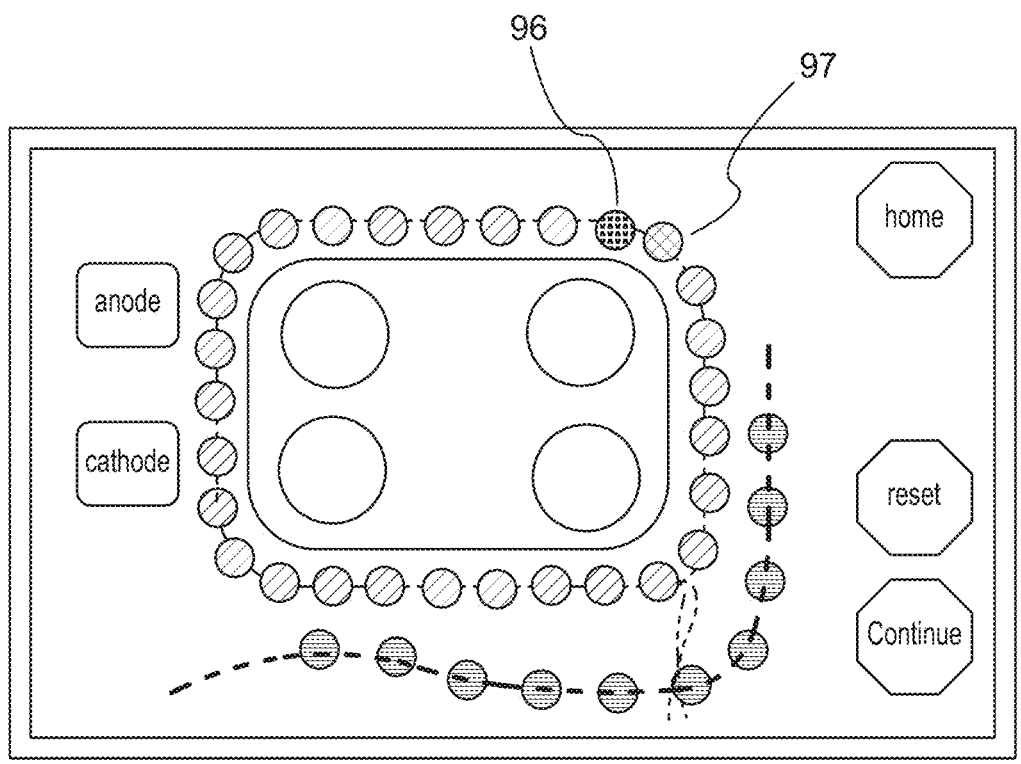
FIG. 11 is a schematic illustration of a user interface that illustrates a method of selecting a single anode electrode and a single selected cathode electrode on the same catheter according to an embodiment.

FIG. 10 shows a portion the user interface of the electroporation system for selection of anode and cathode electrodes, with two catheters connected to the system. One of the catheters is a PV isolation catheter 91 while the other is a multi-electrode catheter 92. The buttons 93 and 94 can implement the selection of marked electrode subsets on the catheters as respectively anode or cathode. Once the selection is made, the appropriate electrodes are colored differently to indicate anode or cathode electrode as shown marked respectively as 96 and 97 in FIG. 11.

Figure 12:
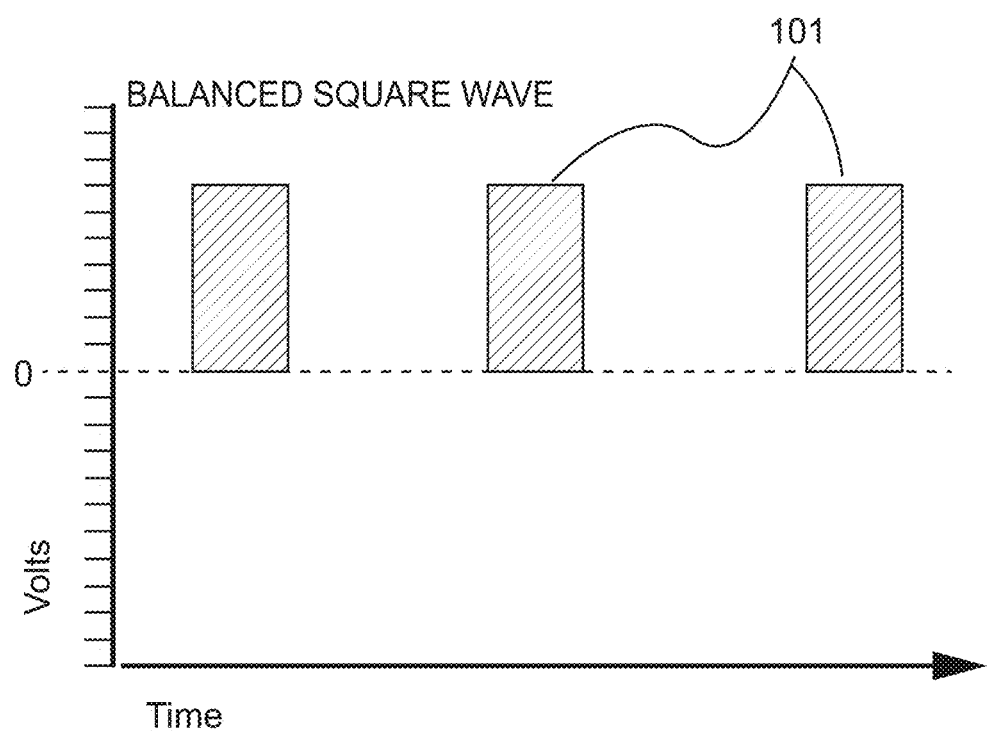
FIG. 12 is a schematic illustration of a waveform generated by the irreversible electroporation system and methods according to an embodiment, showing a balanced square wave.
Figure 13:
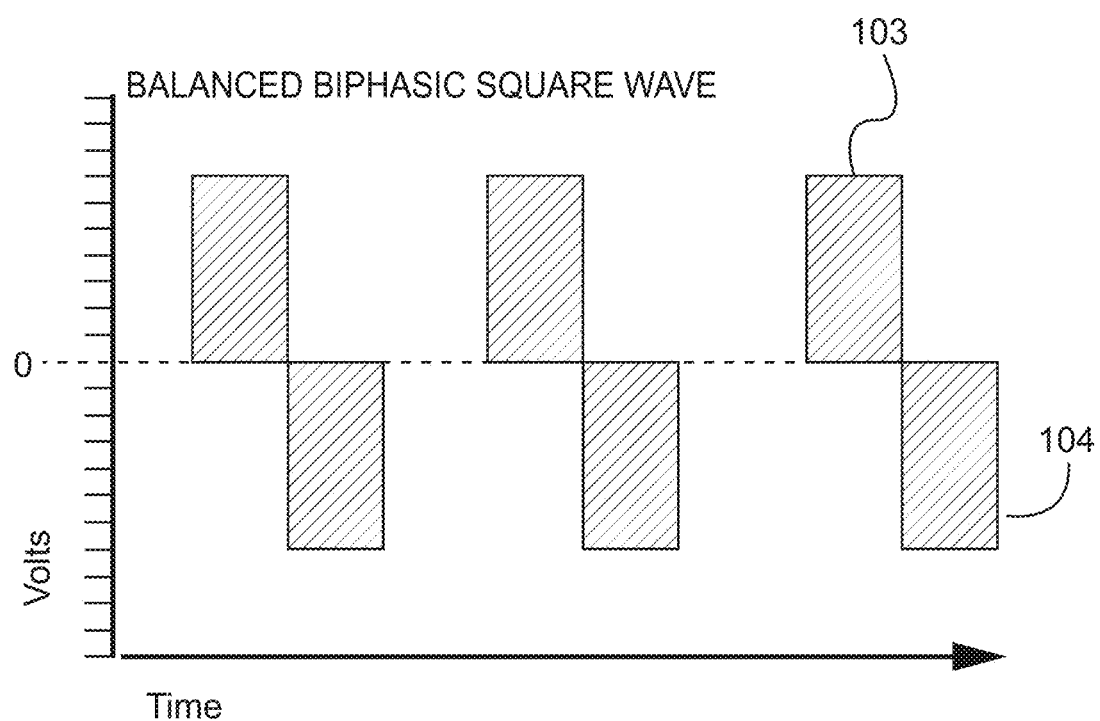
FIG. 13 is a schematic illustration of a waveform generated by the irreversible electroporation system and methods according to an embodiment, showing a balanced biphasic square wave.

The controller and generator can output waveforms that can be selected to generate a sequence of voltage pulses in either monophasic or biphasic forms and with either constant or progressively changing amplitudes. FIG. 12 shows a rectangular wave pulse train where the pulses 101 have a uniform height or maximum voltage. FIG. 13 shows an example of a balanced biphasic rectangular pulse train, where each positive voltage pulse such as 103 is immediately followed by a negative voltage pulse such as 104 of equal amplitude and opposite sign. While in this example the biphasic pulses are balanced with equal amplitudes of the positive and negative voltages, in other embodiments an unbalanced biphasic waveform could also be used as may be convenient for a given application.

Figure 14:
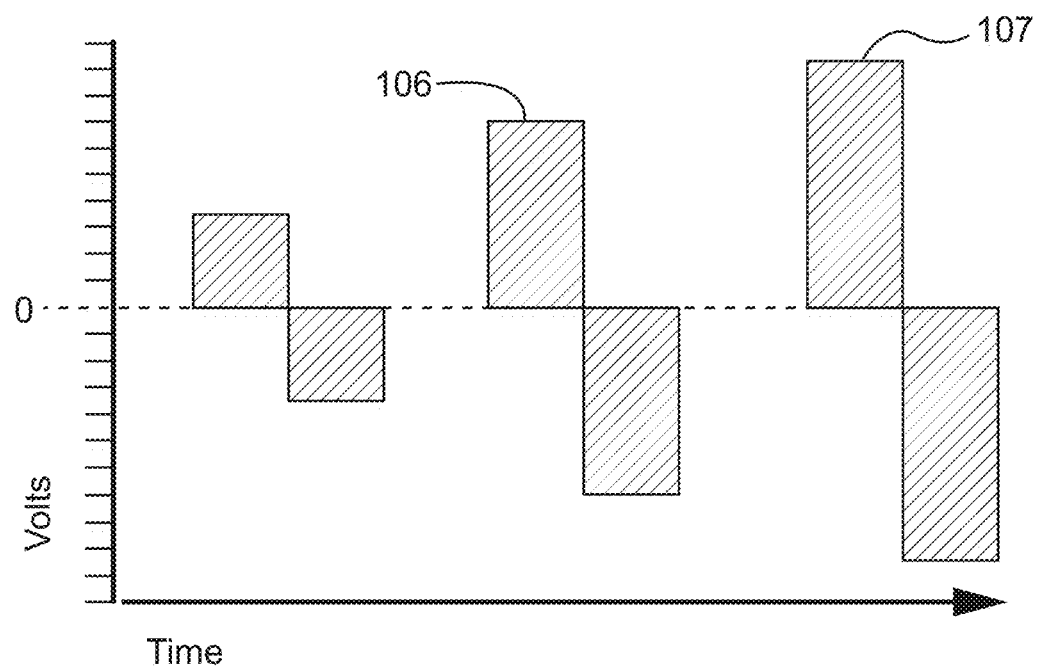
FIG. 14 is a schematic illustration of a waveform generated by the irreversible electroporation system and methods according to an embodiment, showing a progressive balanced biphasic square wave.

Yet another example of a waveform or pulse shape that can be generated by the system is illustrated in FIG. 14, which shows a progressive balanced rectangular pulse train, where each distinct biphasic pulse has equal-amplitude positive and negative voltages, but each pulse such as 107 is larger in amplitude than its immediate predecessor 106. Other variations such as a progressive unbalanced rectangular pulse train, or indeed a wide variety of other variations of pulse amplitude with respect to time can be conceived and implemented by those skilled in the art based on the teachings herein.

The time duration of each irreversible electroporation rectangular voltage pulse could lie in the range from 1 nanosecond to 10 milliseconds, with the range 10 microseconds to 1 millisecond being more preferable and the range 50 microseconds to 300 microseconds being still more preferable. The time interval between successive pulses of a pulse train could be in the range of 10 microseconds to 1 millisecond, with the range 50 microseconds to 300 microseconds being more preferable. The number of pulses applied in a single pulse train (with delays between individual pulses lying in the ranges just mentioned) can range from 1 to 100, with the range 1 to 10 being more preferable. As described in the foregoing, a pulse train can be driven by a user-controlled switch or button, in one embodiment preferably mounted on a hand-held joystick-like device. In one mode of operation a pulse train can be generated for every push of such a control button, while in an alternate mode of operation pulse trains can be generated repeatedly during the refractory periods of a set of successive cardiac cycles, for as long as the user-controlled switch or button is engaged by the user.

In one embodiment of a biphasic waveform, a brief pre-polarization pulse can be applied just prior to the application of a polarizing rectangular pulse. The rapid change in electric field in tissue, in addition to the electric field magnitude, driven by this type of pulse application incorporating a pre-polarizing pulse can promote a more rapid and effective tissue ablation in some applications. A schematic diagram of a voltage/signal generator for the purpose of generating such a waveform employing intrinsic amplification of voltage spikes arising from switching is given in FIG. 15. A DC voltage is generated from the discharge of a suitable capacitor bank 111 (powered by a suitable charging circuit that is not shown and that would be familiar to those skilled in the art) with a suitable high-voltage diode or rectifier 112 serving to ensure voltage polarity. While in one embodiment of the signal generator the voltage discharge passes initially through a snubber or transient-suppression circuit 113 that strongly suppresses transients, in an alternate embodiment an alternate signal path is available via a switch unit 116 that detects and lets through a brief initial voltage spike after a possible voltage inversion. The signal then passes through an Insulated Gate Bipolar Transistor (IGBT) high-power switch 115 and is accessible at terminals 117 for connection to catheter electrodes. When no pre-polarizing pulse is required, the switch unit 116 would not be present, and the signal passes (after transient-suppression in the snubber circuit 113) initially through a Metal Oxide Semiconductor Field Effect Transistor (MOSFET) switch 114 before passing through the IGBT switch 115. The IGBT interfaces better with a wider range of load impedances (from tissue), while the faster switching speed of the MOSFET can drive suitably fast turn-on/turn-off of the IGBT switch, so that using them in the sequence shown in FIG. 15 can be advantageous.

In order to generate a sequence of rectangular pulses, the time constant associated with the capacitor bank discharge is chosen to be significantly longer than an individual pulse duration. If the charging circuit of the capacitor bank is much more rapid, a sequence of very highly rectangular pulses can be generated from repeated capacitor bank discharges. As shown in FIG. 16, when a capacitor bank is suddenly discharged by closing a switch, the voltage can briefly be amplified and spike as indicated by 122 before settling to a normal discharge pattern 121. The inductance of leads connected to the capacitor forms a tank circuit with the capacitor, and in many cases this tank circuit is rapidly driven to resonance by the discharge, leading to the voltage amplification seen in the spiking behavior 122. Indeed, by suitably controlling lead inductance and resistance, the extent of spike generated (spike amplitude and duration) can be further controlled. Such additional inductance/resistance or spike control circuitry can be included in the switch unit 116 shown in FIG. 15. Thus the switch 116 plays a gatekeeping role akin to the notion of "Maxwell's demon" in statistical physics, allowing the passage of some types of intrinsically amplified voltage spikes, and accordingly the signal generator of FIG. 15 can also be termed a Maxwell amplifier.

Figure 15:
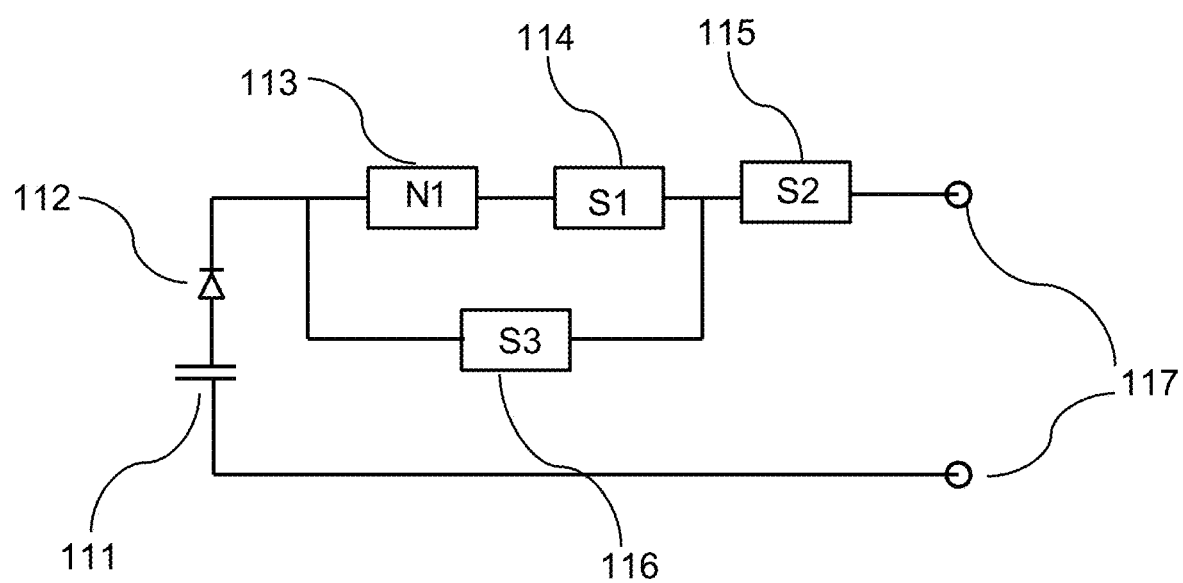
FIG. 15 is a schematic illustration of a signal generator according to an embodiment, showing a capacitor bank connected to a set of switches.
Figure 16:
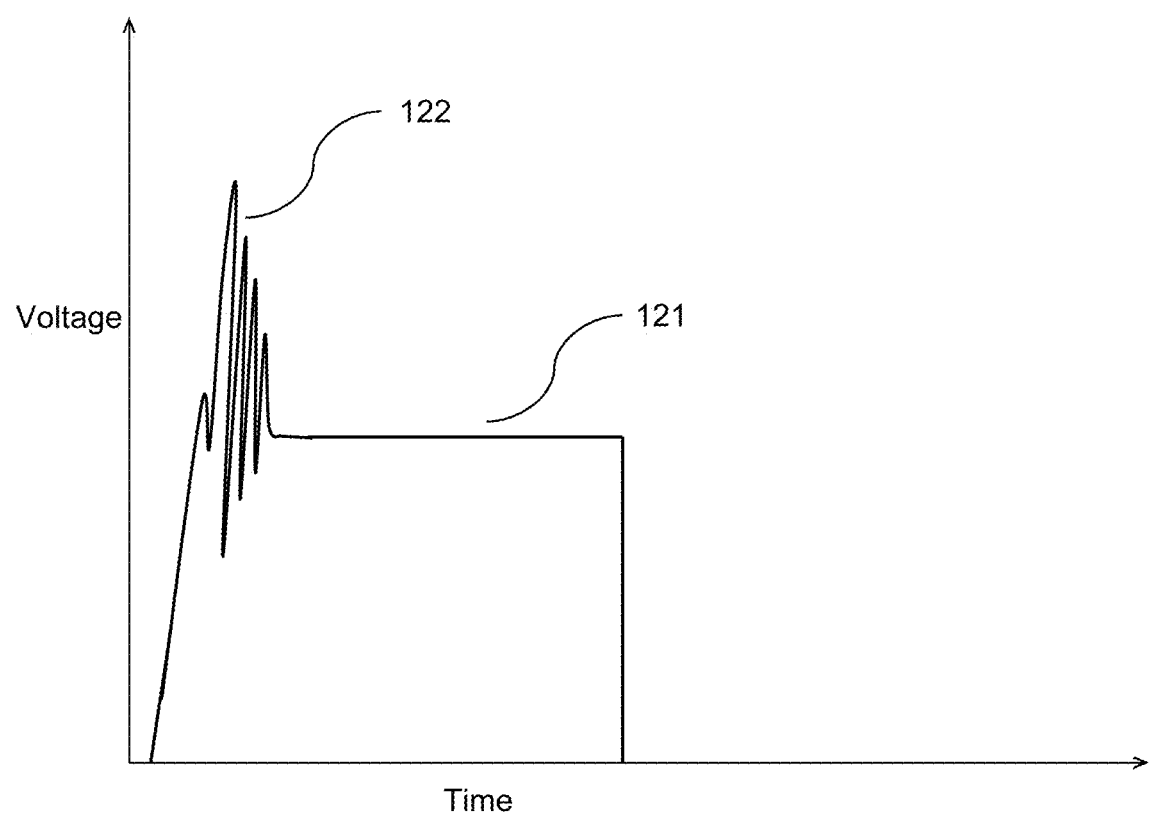
FIG. 16 is a schematic illustration of a voltage pulse-time plot produced by a high voltage DC signal generator according to an embodiment.
Figure 17:
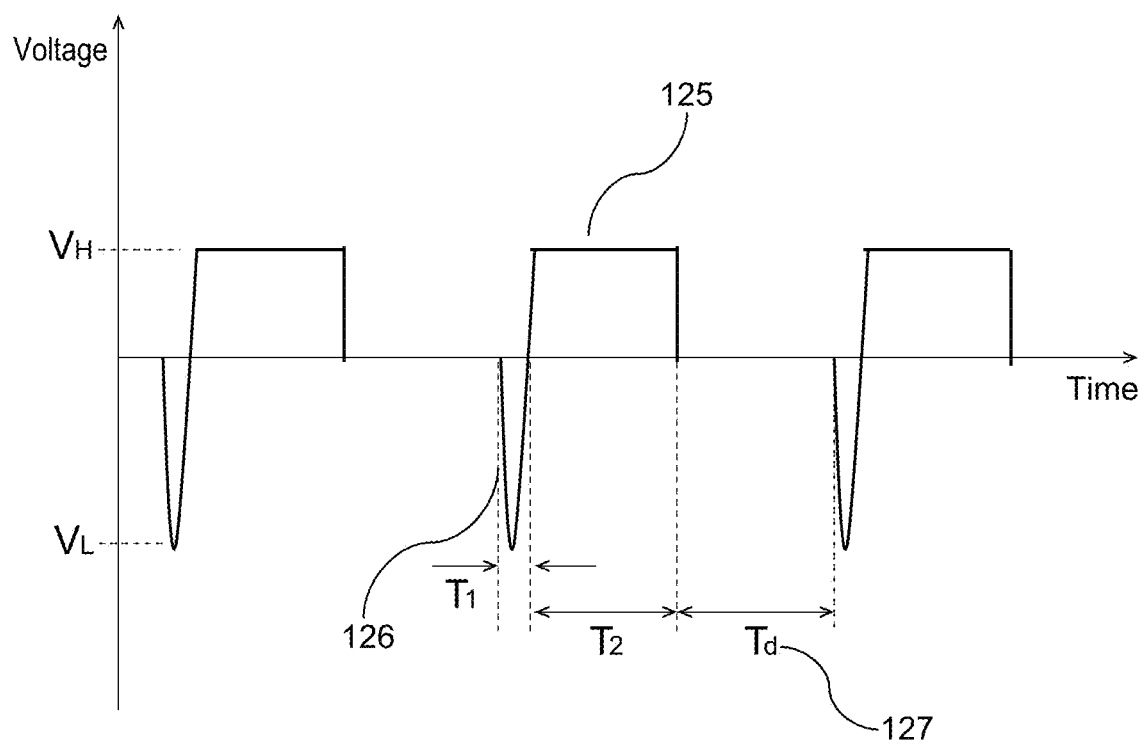
FIG. 17 is a schematic depiction of a sequence of three biphasic pulses delivered by a voltage generator and using methods according to an embodiment, showing a pre-polarizing negative voltage pulse followed by a positive polarizing pulse.

A schematic representation of a biphasic pulse with pre-polarization is shown in FIG. 17, where each rectangular polarizing pulse such as 125 is preceded by a pre-polarizing negative voltage spike 126 derived from transient spiking from a generator of the type shown in FIG. 15. The value of the negative spike voltage peak VL could be determined by the spike control circuitry of the switch unit 116 as discussed above. The biphasic pulses involve a time duration Ti for the pre-polarizing spike, a duration T2 for the rectangular polarizing pulse, with a time delay Ta indicated by 127 in FIG. 17 between successive biphasic pulses. Typical values of T2 could be of the order of 100 microseconds, while Ti could lie in the range 5 microseconds to 50 microseconds and the delay time Ta could be in the range 100 microseconds to 300 microseconds. All of these parameters can be determined by the design of the signal generator, and in various embodiments could also be determined by user control as may be convenient for a given clinical application. The specific examples and descriptions herein are exemplary in nature and variations can be developed by those skilled in the art based on the material taught herein without departing from the scope of the embodiments described herein.

A catheter device for focal ablation with the electroporation system according to an embodiment is shown schematically in FIG. 18A. The focal ablation catheter 131 has two electrodes disposed in the distal section of the catheter, with a relatively proximally placed cathode electrode 133 of length Li exposed on the catheter shaft and a relatively distally placed anode electrode 134 of length L2 mounted on the inner section of the shaft. The catheter shaft is made of a material with high dielectric strength such as for example a polymer comprising Teflon. Thus the distal electrode 134 is covered by the polymeric shaft and is not exposed to the blood pool on the shaft exterior. Both electrodes are metallic, and in one embodiment the anode could be poly-metallic in construction, for example comprising regions of Titanium and regions of Platinum.

Figure 18C:
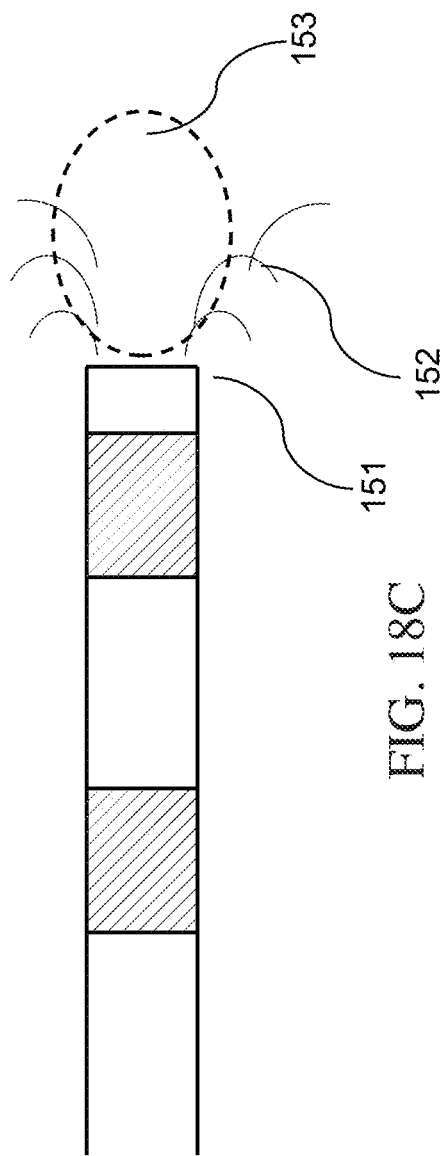
FIG. 18C is a schematic illustration of a distal portion of a catheter according to an embodiment, where electric field lines near the distal end of the catheter are schematically shown together with a region of focal ablation in tissue.

As shown in FIG. 18B, the anode 141 is recessed from the distal tip, and could be placed with its distal portion between 0.5 mm and 10 mm away from the distal end of the catheter. While the recessed and interior placement of the anode electrode is counterintuitive, it can be an effective means of enhancing electroporation efficacy and safety selectively for focal ablation. As indicated in the FIG., the schematically depicted (negative) current density flowing from the cathode to the anode indicated by the stream of arrows 142 bends around the distal edge 143 of the catheter shaft resulting in a region of high curvature of the current density, and correspondingly curved electric field lines as well. If the anode electrode is recessed, the highest curvature region at the edge of the electrode where the strongest electric field occurs is also displaced proximally, so that the electric field around the distal tip of the catheter itself is not so large as to cause any increased local heating, while remaining large enough to cause irreversible electroporation. FIG. 18C schematically shows electric field lines 152 as they curve to enter the distal catheter end 151, resulting in a zone or region 153 distal to the catheter with a relatively uniform electric field. The electric field in this region would not be as uniform with a standard, externally placed electrode on the catheter, and further would generally have regions of very high intensity. The recessed interior placement of the distal electrode therefore results in superior and safe electroporation ablation delivery for focal ablation in a selective zone distal to the catheter tip. While in one embodiment the anode electrode can be a hollow ring, in other embodiments it could have a different form such as a cylinder with multiple longitudinal holes or channels.

Figure 18D:
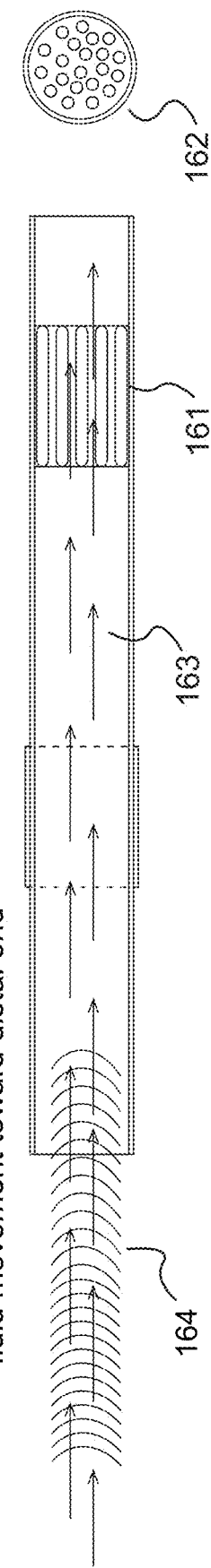
FIG. 18D is a schematic illustration of a distal portion of a catheter according to an embodiment, where the catheter lumen has flowing fluid, possibly with ultrasonic waves conducted through the fluid, and the distal anode electrode has channels for fluid flow to exit the distal end of the catheter.

In some embodiments, the interior lumen of the catheter can carry a fluid delivered out through the distal end of the catheter. The fluid can be an ionic fluid such as isotonic or hypertonic saline and can enhance electrical conductivity in the distal region of the catheter and beyond the distal end ensuring a proper and more uniform distribution of local electric field in a distal region around the catheter. As shown in FIG. 18D, the inner lumen 163 of the catheter carries a flowing fluid indicated by the arrows, while the anode 161 is in the shape of a cylinder that has longitudinal channels through which fluid can flow. The anode electrode is shown in cross section 162 where the multiple through-channels are visible. The saline or ionic fluid delivered through the channels can act as an ion bridge through which good electrical current conduction is possible in the vicinity of the catheter's distal end, resulting in a more uniform distribution of local electric field and electroporation energy delivery. Further, the flow of saline fluid itself can dislodge tissue debris or any bubbles generated by the electroporation-driven breakdown of tissue in the region around the distal catheter tip. In one embodiment, ultrasonic waves schematically shown as 164 in FIG. 18D can be applied to the fluid to further ensure that any bubbles that may be lodged on the catheter surface in its distal region are dislodged, again for purposes of maintaining relative uniformity of the local electric field. The ultrasonic waves or ultrasound through the fluid can be generated by suitable piezoelectric transducers mounted more proximally along the shaft of the catheter, or even within the catheter handle. In one embodiment, ultrasound generation is coordinated with electroporation DC voltage application so that the kinetic energy of focused ultrasound is available "on demand."

Figure 19A:
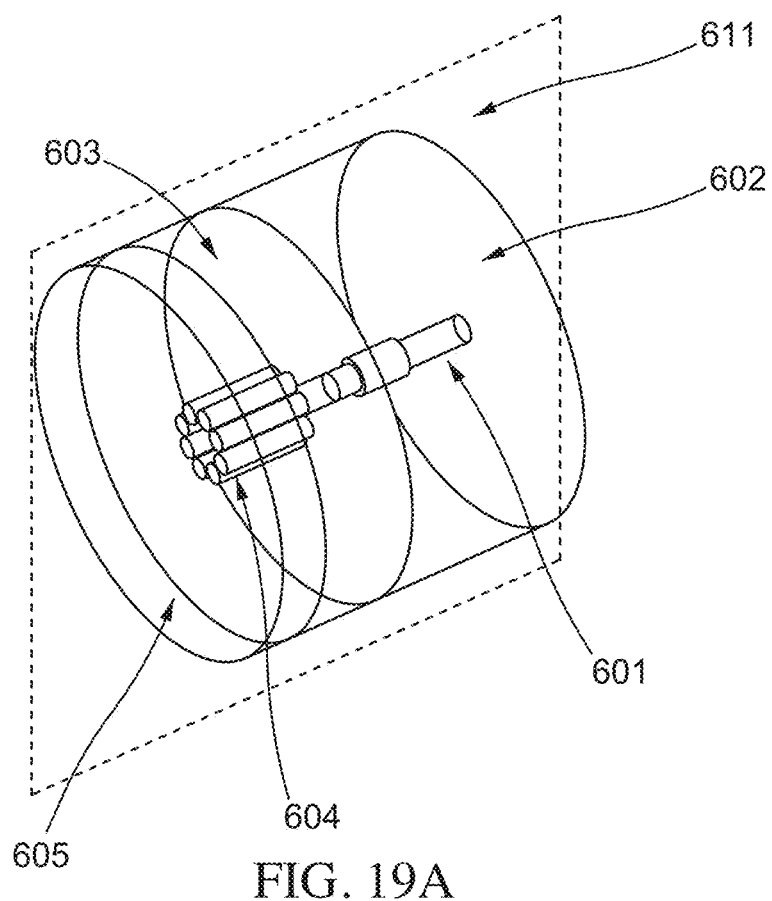
FIG. 19A is an illustration of the simulation geometry showing a geometric model of the distal portion of a catheter and surrounding tissue types.
Figure 19B:
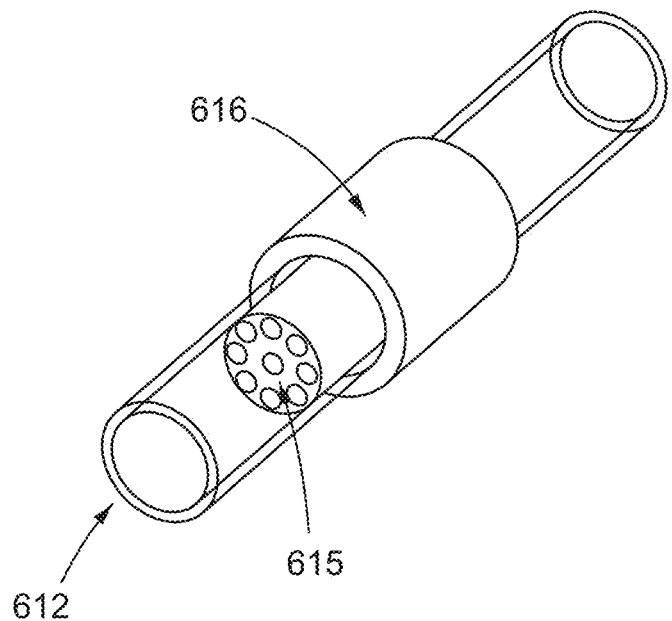
FIG. 19B is an illustration of the distal portion of a catheter with a proximal electrode disposed externally on the shaft of the catheter and a distal electrode that is recessed and disposed on the inner side of the shaft of the catheter.
Figure 19C:
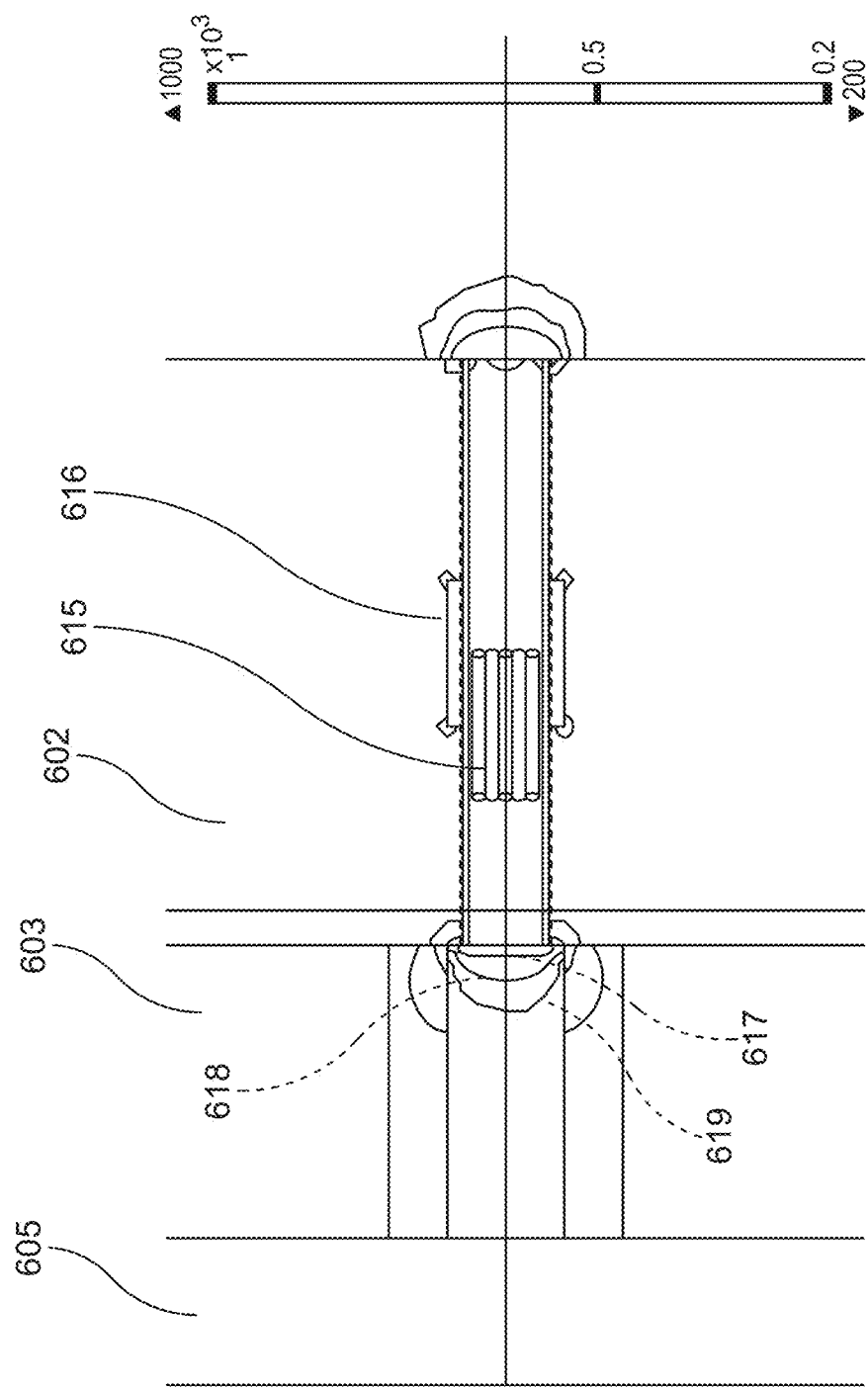
FIG. 19C is an illustration of a longitudinal cross-section of the simulation geometry showing distal catheter geometry and tissue geometry together with electric field intensity contours for the case when the proximal electrode is disposed externally on the shaft of the catheter and the distal electrode is recessed and disposed on the inner side of the shaft of the catheter, according to an embodiment.

The above statements of the advantages of the recessed inner electrode for the focal ablation catheter have been verified by the inventors in physically realistic simulations. FIG. 19A shows a simulation geometry of a catheter 601 in a blood pool region 602 and abutting a myocardium region 603 adjacent to a pericardial region 605, all regions being assumed cylindrical for the simulation; the section or plane 611 was chosen to plot electric field intensity contours. Further the myocardium region has a region of scar tissue 604 distal to the catheter. FIG. 19B shows the catheter's distal region with distal tip 612, distal (anode) recessed electrode 615 mounted internal to the shaft, and a proximal (cathode) electrode 616. With a DC voltage of 1000 Volts applied between the electrodes and using realistic physical property values, the resulting electric field intensity contours are illustrated in FIG. 19C, which shows the geometry and the contours in the section 611 of FIG. 19A. The cathode 616 and recessed anode 615 are indicated in FIG. 19C, as are the blood pool region 602, the myocardium region 603 and the pericardial region 605. The electric field intensity contours corresponding to 1000 Volts/cm, 500 Volts/cm and 200 Volts/cm respectively are shown as contours 617, 618 and 619 respectively.

Figure 19D:
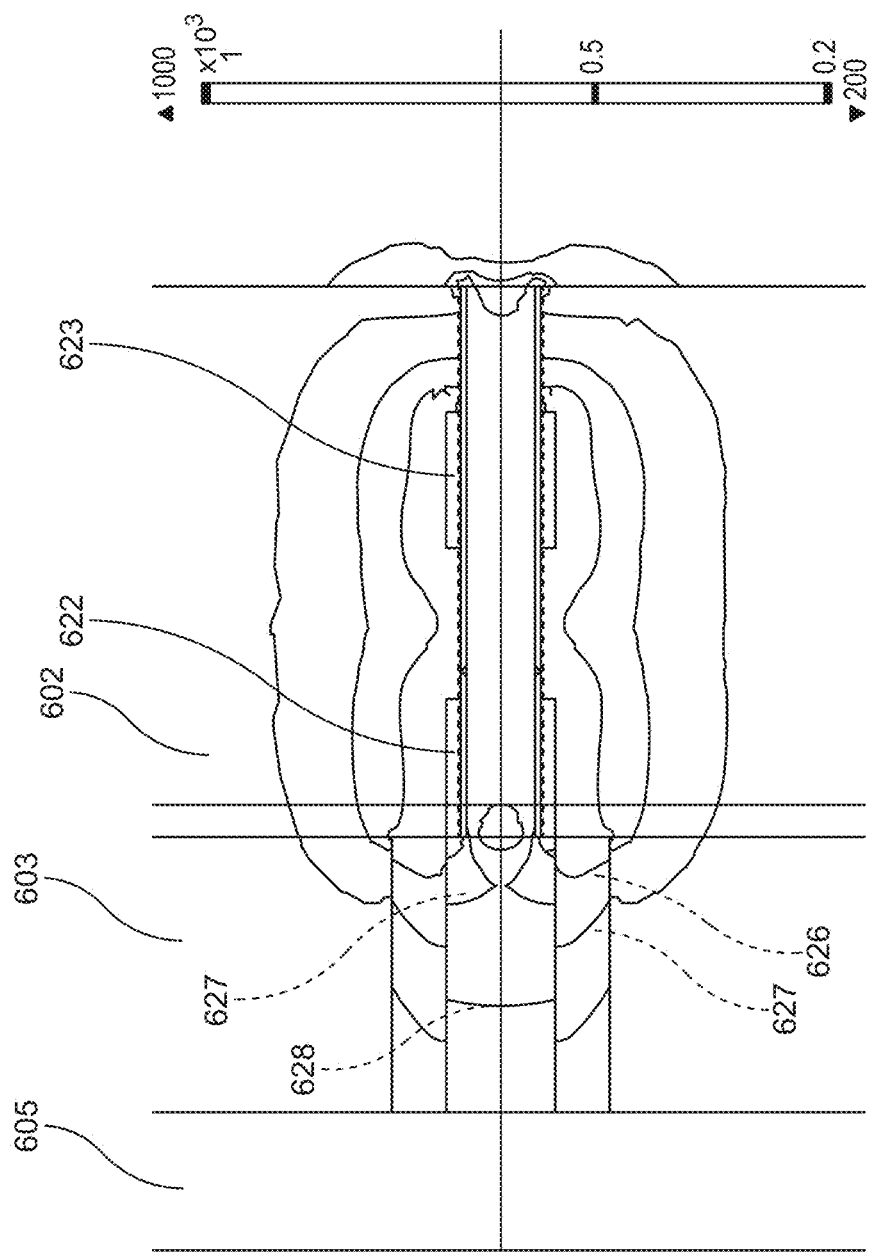
FIG. 19D is an illustration of a longitudinal cross-section of the simulation geometry showing distal catheter geometry and tissue geometry together with electric field intensity contours for the case when the proximal and distal electrodes are both disposed externally on the shaft of the catheter, according to an embodiment.

FIG. 19D repeats the electric field simulation for a catheter with both electrodes mounted externally, showing the distal anode 622 and proximal cathode 623 in the same tissue geometry. As before, with a DC voltage of 1000 Volts applied between the electrodes and using the same realistic physical property values, the resulting electric field intensity contours corresponding to 1000 Volts/cm, 500 Volts/cm and 200 Volts/cm respectively are shown as contours 626, 627 and 628 respectively.

Comparing the intensity contours of FIG. 19C and FIG. 19D, it is clear that the former FIG. shows a relatively more uniform intensity distribution in the myocardium region where excessively large electric field values (500 Volts/cm or more) are present to a much lesser extent, mitigating the possibility of locally large electric current densities and corresponding temperature increases.

The focal ablation catheter described above in various embodiments could be used in cardiac applications such as ablation delivery to treat Ventricular Tachycardia (VT), where targeted ablation delivery could be of great benefit. In one embodiment, the length L2 of the distal anode electrode could be significantly longer than the length Li of the proximal cathode electrode. The ratio L2/Li could have a value of at least 1.3, more preferably lie in the range 1.3 to 10, and still more preferably in the range 2 to 5. The increased surface area of the exposed inner surface of the anode electrode can serve to reduce the current density near it, thereby enhancing safety and enhancing the efficacy of ion bridging current transfer with the saline fluid infusion. In addition or as an alternate method to reduce high current density due to exposed metal regions with high curvature, the edges of the electrode can be beveled or rounded to ensure that there are no sharp corners or regions with high curvature.

Thus, the methods described herein allow for a variety of approaches in the context of cardiac ablation. Considering for example the treatment of Ventricular Tachycardia (VT) as a clinical application, electroporation ablation of cardiac tissue could be performed across a pair of nearby electrodes respectively on one or more epicardially placed catheters in one embodiment. In an alternate embodiment, a single focal ablation endocardial catheter such as described above can be used to ablate on the endocardial side of a cardiac chamber. In still another alternate embodiment, a bipolar pair of electrodes on different catheters, one placed endocardially and the other epicardially could be used to drive irreversible electroporation.

Figure 20:
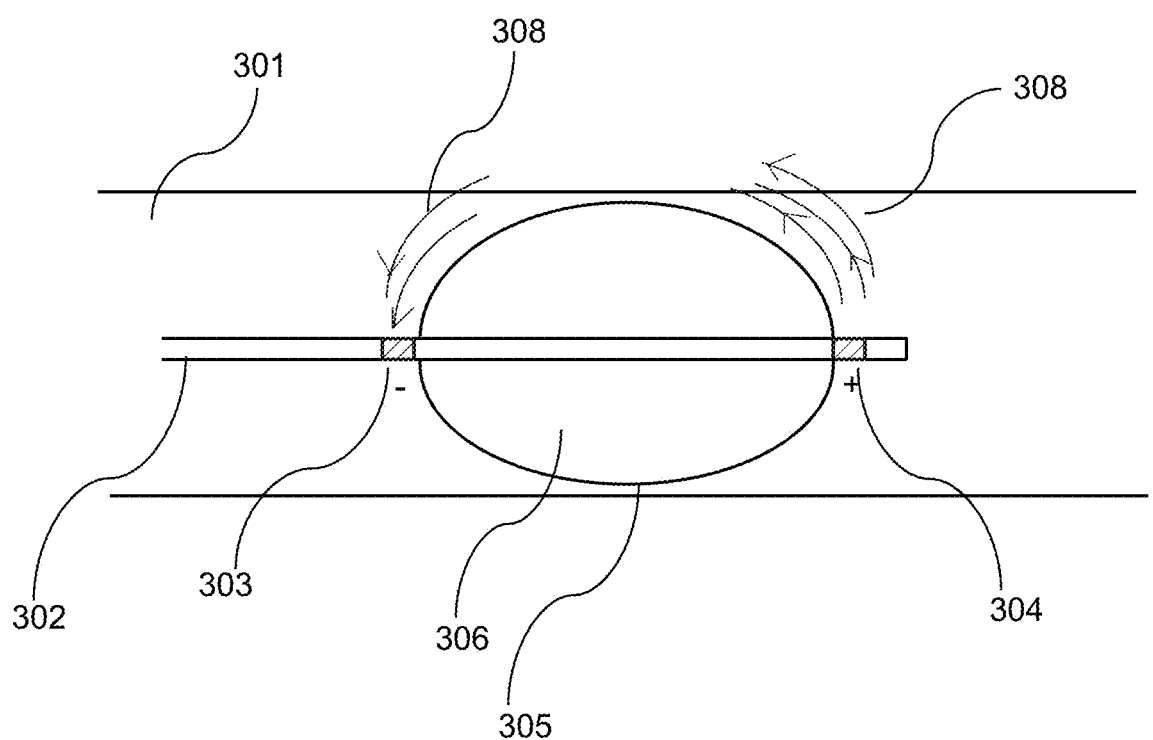
FIG. 20 is a schematic illustration of a balloon catheter according to an embodiment, where a balloon structure with an insulating exterior is located between anode and cathode electrodes for electroporation voltage delivery.

A balloon ablation device for use with the electroporation system according to an embodiment is schematically illustrated in FIG. 20. While the device is shown to be situated in a blood vessel 301, it can also be used in other anatomical areas such as a cardiac ventricle. The device shaft 302 has an inflatable balloon 306 disposed in its distal portion. On either side of the balloon and mounted on the shaft are a proximal cathode electrode 303 and a distal anode electrode 304. The balloon surface 305 is coated with a thin layer of a good insulator such as a biocompatible metal oxide (for example, aluminum oxide). When air is pumped in through the catheter shaft lumen and through appropriate openings (not shown) from the shaft into the balloon, the balloon can inflate, as the inflated shape in FIG. 20 depicts. In ventricular applications such as cardiac ablation for VT, the balloon can serve to displace collateral structures away from the distal end of the catheter. Since the balloon surface is an insulator, when a DC voltage is applied between the electrodes, the current flow between electrodes and through the tissue is deflected around the balloon. The electric field is also correspondingly deflected around the surface of the balloon, and curves outward and can extend into the wall of the blood vessel, as shown by the schematic electric field lines 308 in the FIG. In one embodiment, the distal electrode 304 can be mounted on the outside of the shaft with external surface exposed, for intravascular ablation applications such as for example peripheral vascular applications for treatment of atherosclerosis where it is desired to ablate the vessel wall region or clear deposits. In an alternate embodiment, the distal electrode 304 can be mounted on the inner side of the catheter shaft, so that the metal electrode is internally exposed. Furthermore, the distal electrode could be recessed from the distal tip, as schematically shown in FIG. 20. Such a device could be used in focal ablation applications.

Figure 21A:
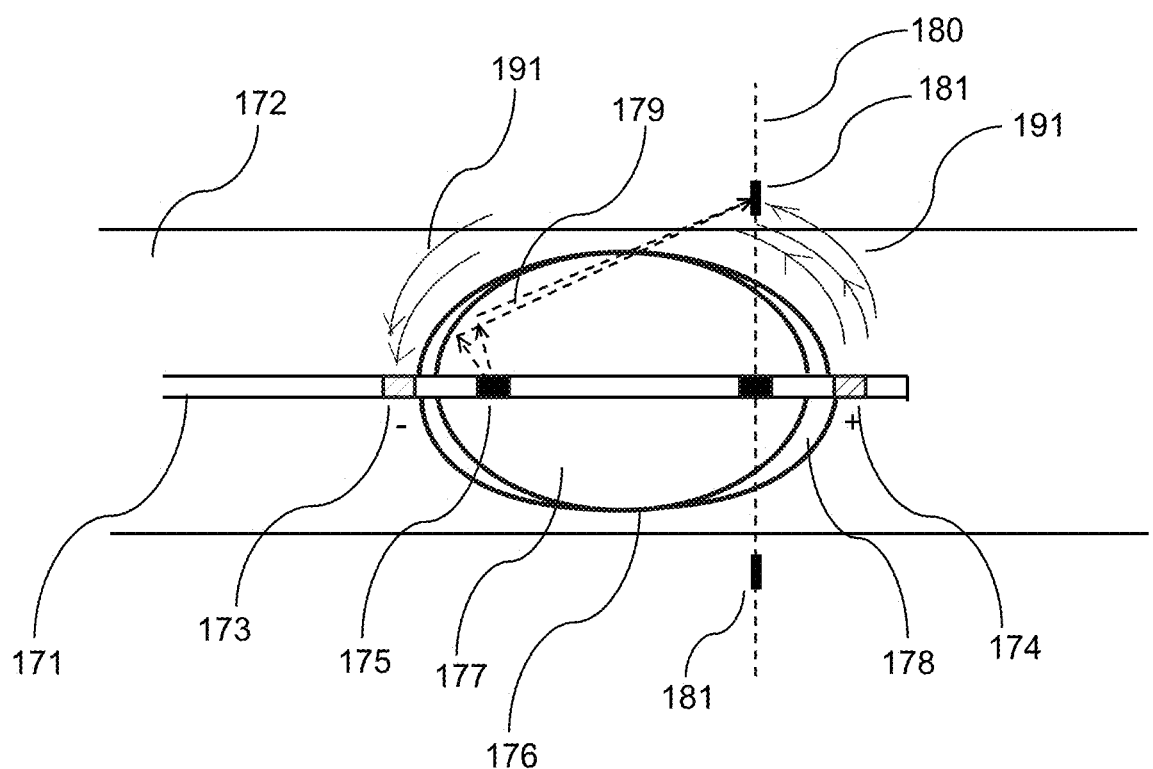
FIG. 21A is a schematic illustration of a balloon catheter according to an embodiment, where a balloon structure with an insulating exterior and with at least one ultrasonic transducer is located between anode and cathode electrodes for electroporation voltage delivery.
Figure 21B:
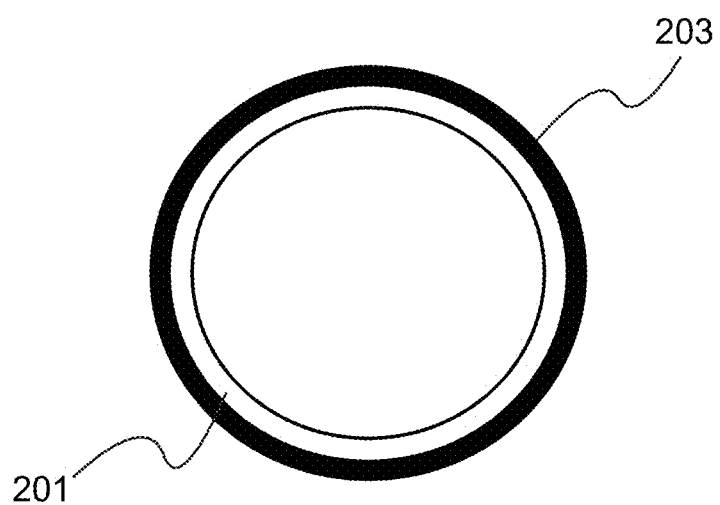
FIG. 21B is a schematic illustration of a balloon catheter according to an embodiment, where an annular ablation region abutting a vessel is shown.

An alternate preferred embodiment of a balloon ablation device for use with the electroporation system according to an embodiment is shown schematically in FIG. 21A. As before, while the device is shown to be situated in a blood vessel 172, it can also be used in other anatomical areas such as a cardiac ventricle. The device shaft 171 has an inflatable balloon 177 disposed in its distal portion. On either side of the balloon and mounted on the shaft are a proximal cathode electrode 173 and a distal anode electrode 174. The balloon surface 176 is coated with a thin layer of a good insulator such as a biocompatible metal oxide (for example, aluminum oxide). When fluid is pumped in through the catheter shaft lumen, the balloon can inflate, as the inflated shape in FIG. 21A depicts. The region of the shaft within the balloon can have at least one ultrasonic transducer 175 mounted thereon. Further, while the interior of the balloon is inflated with fluid, the wall 178 of the balloon has a varying cross section and is filled with a gas such as air. Thus there is a liquid-gas interface at the wall of the balloon. This interface can act as a mirror or reflecting surface for ultrasound. As illustrated in the FIG., ultrasound rays 179 emitted by the transducer 175 are reflected at the wall of the balloon and are subsequently focused on a ring-like region, shown with its annular regions 181 in a plane 180 and viewed edge-on in the illustration. The annular region external to the balloon where the ultrasound is focused is shown in FIG. 21B as the dark annulus 203 surrounding the vessel wall 201, shown in cross section. When high-intensity ultrasound generated by the transducer in the catheter is focused in this manner, its energy is deposited in the annulus as heat and raises temperature locally. The irreversible electroporation threshold of tissue is temperature dependent and is lowered with increasing temperature. Thus in the annular region where temperature is increased due to the focused ultrasound, the electroporation threshold is decreased, and a relatively weaker electric field in this region can still generate irreversible electroporation, permitting selective tissue ablation.

As before, in ventricular applications such as cardiac ablation for VT, the balloon can serve to displace collateral structures away from the distal end of the catheter. Since the balloon surface is an insulator, when a DC voltage is applied between the electrodes, the current flow between electrodes and through the tissue is deflected around the balloon. The electric field is also correspondingly deflected around the surface of the balloon, and curves outward and can extend into the wall of the blood vessel, as shown by the schematic electric field lines 191 in the FIG. With the lowered irreversible electroporation threshold in the annular region of focused ultrasound in the vessel wall, the electric field in the annular region is sufficient to selectively drive irreversible electroporation. In one embodiment, the distal electrode 174 can be mounted on the outside of the shaft with external surface exposed, for intravascular ablation applications such as for example peripheral vascular applications for treatment of atherosclerosis where it is desired to ablate the vessel wall region or clear deposits. In an alternate embodiment, the distal electrode 174 can be mounted on the inner side of the catheter shaft, so that the metal electrode is internally exposed. Furthermore, the distal electrode could be recessed from the distal tip, as schematically shown in FIG. 21A. Such a device could be used in focal ablation applications.

Figure 22:
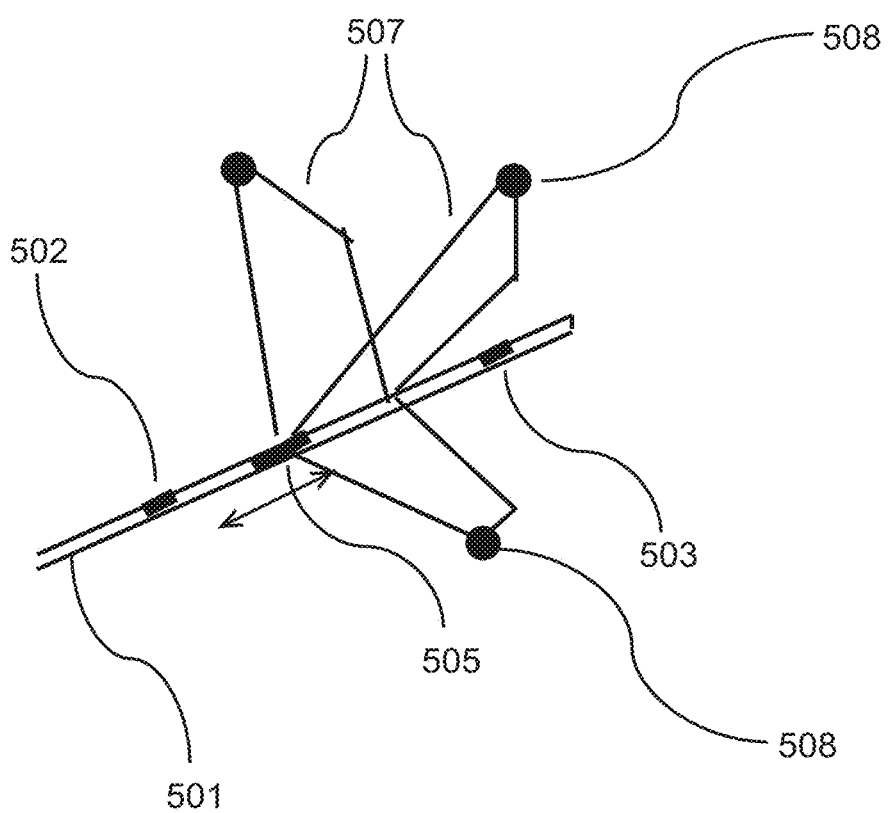
FIG. 22 is a schematic illustration of a basket ablation catheter for electroporation energy delivery according to an embodiment.

While the specific embodiment of the balloon ablation device described above utilizes high-intensity focused ultrasound to selectively generate temperature increases in a given region in order to decrease the electroporation threshold, it must be noted that alternate energy delivery mechanisms such as microwaves could be utilized for the purpose of increasing tissue temperature by energy deposition in order to decrease the irreversible electroporation threshold electric field. The balloon ablation devices described in the foregoing could also be used in pulmonary outflow tract applications to treat pulmonary hypertension, or in eosophageal or gastrointestinal applications where tissue ablation is an appropriate therapy. An ablation device for irreversible electroporation in the form of an expanding basket catheter is schematically illustrated in FIG. 22. Mounted on the shaft 501 of the device is a sliding member 505 which is attached to a system of struts 507. While the system of struts is initially substantially aligned with the length of the shaft in a folded configuration (not shown), it can unfold or open out like an umbrella by movement of the sliding member 505 along the shaft, resulting in the basket-like unfolded structure shown in FIG. 22. For purposes of clarity, the system of struts is only partially shown in the figure. The basket construction or set of expanding struts can comprise a superelastic alloy such as for instance an alloy of Nickel and Titanium often called Nitinol®; such a construction can be of use in a large vessel where a significant amount of expansion could be called for. On either side of the basket-like structure and disposed along the shaft are two electrodes 502 and 503. Bead-like electrodes 508 are present at corners of the strut assembly. The device be guided to a desired location inside a large vascular or other anatomical vessel (for example, the pulmonary outflow tract), positioned suitably and then unfolded. Subsequently, irreversible electroporation ablation can be applied with the electrodes on the basket device.

In one embodiment the basket catheter with struts folded can have a lumen for passage of a suitable guidewire which could be used as a delivery system for appropriate placement of the basket catheter. Various choices of electrode configurations for ablation are possible for this device. In one preferred embodiment, either of electrodes 502 or 503 is selected as cathode, while the beads 508 are selected as anodes. With such a choice, a region of vessel wall that is located just proximal to or just distal to the beads can be selectively ablated, depending on whether electrode 502 or electrode 503 respectively is activated as cathode. The rounded shape of the beads and their location on the outer edge of the basket (and thus close to the vessel wall) results in good ablation characteristics at the vessel wall. The voltage applied can be suitably selected so that an appropriate electric field is generated in the ablative region near the bead electrodes. In alternate preferred embodiments, the basket catheter can further incorporate energy sources such as focused ultrasound or microwaves in order to selectively raise temperatures in localized regions and thereby lower the irreversible electroporation threshold.

In some embodiments, a method includes identifying, via a selection module of an electrode controller, a set of anode/cathode pairs from a set of electrodes of a multi-electrode catheter. The method can be performed using any suitable controller, such as for example, the controller 900 described above. The multi-electrode catheter is configured to be disposed about a portion of a heart. At least one of the anode/cathode pair including at least one anode electrode and at least one cathode electrode. In other embodiments, however, the anode/cathode pair can include multiple anode electrodes or cathode electrodes. In some embodiments, the identifying can be based on input received from an input/output module of the electrode controller (e.g., manual input). In other embodiments, the identifying can be based on a predetermined schedule of electrodes. In yet other embodiments, the identifying can be performed automatically based on an impedance map as described herein.

The method further includes conveying a pacing signal to a pacing lead configured to be operatively coupled to the heart, and receiving, at a feedback module of the electrode controller, an electrocardiogramal associated with a function of the heart.

The method further includes delivering, via a pulse delivery module of the electrode controller, a pulsed voltage waveform to the plurality of anode/cathode pairs according to a sequential pattern.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various specific examples and embodiments of systems and tools for selective tissue ablation with irreversible electroporation were described in the foregoing for illustrative and exemplary purposes, it should be clear that a wide variety of variations and alternate embodiments could be conceived or constructed by those skilled in the art based on the teachings herein. While specific methods of control and DC voltage application from a generator capable of selective excitation of sets of electrodes were disclosed, persons skilled in the art would recognize that any of a wide variety of other control or user input methods and methods of electrode subset selection etc. can be implemented without departing from the scope of the present invention. Likewise, while the foregoing described a range of specific tools or devices for more effective and selective DC voltage application for irreversible electroporation through ionic fluid irrigation and ultrasonic agitation, including insulating balloon constructions, focal ablation tools, and a basket catheter with a multiplicity of, other device constructions or variations could be implemented by one skilled in the art by employing the principles and teachings disclosed herein without departing from the scope of the present invention, in the treatment of cardiac arrhythmias, in intravascular applications, or a variety of other medical applications.

Furthermore, while the present disclosure describes specific embodiments and tools involving irrigation with saline fluids and the use of temperature to selectively ablate tissue by taking advantage of the temperature-dependence of the threshold of irreversible electroporation, it should be clear to one skilled in the art that a variety of methods and devices for steady fluid delivery, or for tissue heating through the delivery of focused kinetic energy or electromagnetic radiation could be implemented utilizing the methods and principles taught herein without departing from the scope of the present invention.

Where schematics and/or embodiments described above indicate certain components arranged in certain orientations or positions, the arrangement of components may be modified. For example, although the controller 900 is shown as optionally including the pacing module 902, in other embodiments, the controller 900 can interface with a separate pacing module. Similarly, where methods and/or events described above indicate certain events and/or procedures occurring in certain order, the ordering of certain events and/or procedures may be modified.

Although various embodiments have been described as having particular features and/or combinations of components, other embodiments are possible having a combination of any features and/or components from any of embodiments as discussed above.

The invention claimed is:

1. A system for conducting bipolar pulsed field ablation of cardiac tissue through a process of irreversible electroporation, the system comprising:
   a medical device comprising a catheter defining a proximal end and a distal end, the catheter comprising a plurality of electrodes disposed at the distal end;
   an electroporation system configured for electrical communication with the plurality of electrodes of the medical device via one or more leads extending within the catheter, the electroporation system also comprising a generator;
   wherein the generator is configured to generate at least one sequence of biphasic voltage pulses having at least one amplitude, the at least one amplitude between about 0.5 kV and about 10 kV;
   wherein the electroporation system is configured to apply the at least one sequence of biphasic voltage pulses to the plurality of electrodes such that current associated with at least one first voltage pulse from the at least one sequence of voltage pulses flows between a first anode electrode and first and second cathode electrodes of the plurality of electrodes to thereby generate an electric field of sufficient strength to cause irreversible electroporation of the cardiac tissue proximate the distal end of the catheter;
   wherein the electroporation system is configured to apply the at least one sequence of biphasic voltage pulses to the plurality of electrodes such that current associated with at least one second voltage pulse from the at least one sequence of biphasic voltage pulses flows between a second anode electrode and third and fourth cathode electrodes of the plurality of electrodes to thereby generate an electric field of sufficient strength to cause irreversible electroporation of the cardiac tissue proximate the distal end of the catheter, wherein the second anode-electrode differs from the first anode electrode and wherein the third and fourth cathode electrodes differ from the first and second cathode electrodes.

2. The system of claim 1, wherein the generator is configured to generate the at least one sequence of biphasic voltage pulses as square waves having a positive phase and a negative phase.

3. The system of claim 1, wherein the at least one amplitude is between about 1 kV and about 2 kV.

4. The system of claim 1, wherein the electroporation system comprises a user interface, the user interface configured to receive a selection of the first anode electrode and the first and second cathode electrodes of the plurality of electrodes.

5. The system of claim 4, wherein the user interface comprises a touchscreen display.

6. A system for conducting bipolar pulsed field ablation of cardiac tissue through a process of irreversible electroporation, the system comprising:
   a medical device comprising a catheter defining a proximal end and a distal end and a plurality of electrodes disposed at the distal end;
   an electroporation system configured for electrical communication with the plurality of electrodes of the medical device via one or more leads extending within the catheter, wherein the electroporation system comprises a generator and a user interface, the user interface configured to receive a selection by an operator of a first anode electrode from the plurality of electrodes and a plurality of cathode electrodes from the plurality of electrodes;

wherein the generator is configured to generate at least one sequence of biphasic voltage pulses having at least one amplitude between about 0.5 kV and about 10 kV;

wherein the electroporation system is configured to apply one or more voltage pulses from the at least one sequence of biphasic voltage pulses to the first anode electrode and the plurality of cathode electrodes of the plurality of electrodes so that current associated with each of the one or more voltage pulses flows between the first anode electrode and the plurality of cathode electrodes.

7. The system of claim 6, wherein the plurality of cathode electrodes includes two electrodes.

8. The system of claim 6, wherein the catheter further comprises a slidable first member and a second member carrying the plurality of electrodes, the second member having a first end attached to the distal end of the catheter and an opposite second end coupled with the slidable first member.

9. The system of claim 8, wherein the slidable first member is configured to move relative to the distal end of the catheter to cause the second member to move between a first configuration in which the plurality of electrodes are aligned with the length of the catheter and a second configuration in which the plurality of electrodes are disposed radially outward of the catheter.

10. The system of claim 6, wherein the electroporation system is configured to synchronize the generator output with either a paced stimulus applied to a heart or to an external trigger signal.

11. The system of claim 10, wherein the electroporation system is configured to apply the one or more voltage pulses from the at least one-fir-s sequence of biphasic voltage pulses to the first anode electrode and the plurality of cathode electrodes; during predefined intervals from the paced stimulus or the external trigger signal.

12. The system of claim 6, wherein the electroporation system is configured to apply the one or more voltage pulses from the at least one sequence of biphasic voltage pulses to the first anode electrode and the plurality of cathode electrodes of the plurality of electrodes while the remaining electrodes of the plurality of electrodes are inactive.

13. A system for conducting bipolar pulsed field ablation of cardiac tissue through a process of irreversible electroporation, the system comprising:

a medical device comprising a catheter defining a proximal end and a distal end and a plurality of electrodes disposed at the distal end, the plurality of electrodes including at least a first electrode, a second electrode, and a third electrode;

an electroporation system in electrical communication with the plurality of electrodes of the medical device via one or more leads extending within the catheter, the electroporation system further comprising a generator;

wherein the generator is configured to generate at least one sequence of biphasic voltage pulses having at least one amplitude, the at least one amplitude between about 0.5 kV and about 10 kV;

wherein the electroporation system is configured to apply at least one first voltage pulse from the sequence of biphasic voltage pulses concurrently between the first electrode as an anode electrode and the second and third electrodes as cathode electrodes to thereby generate an electric field of sufficient strength to cause irreversible electroporation of the cardiac tissue proximate the distal end of the catheter.

14. The system of claim 13, wherein the electroporation system is configured to apply at least one second voltage pulse from the at least one sequence of biphasic voltage pulses concurrently between the second electrode as an anode electrode and the first and third electrodes as cathode electrodes.

15. The system of claim 13, wherein the plurality of electrodes includes nine or more electrodes.

16. The system of claim 13, wherein the electroporation system comprises a user interface and is configured to display on the user interface a representation of the plurality of electrodes and an indication of the electrodes to be used in ablation.

17. The system of claim 16, wherein the electroporation system is configured to display on the user interface an impedance detected at each electrode of the plurality of electrodes.

18. The system of claim 16, wherein the user interface is configured to receive a selection of the first, second, and third electrodes.

19. The system of claim 13, wherein the at least one first voltage pulse comprises multiple voltage pulses.

* * * * *